(12) United States Patent
Silverstein et al.

(10) Patent No.: US 11,386,997 B2
(45) Date of Patent: Jul. 12, 2022

(54) SYSTEM AND METHOD FOR PROVIDING NOTIFICATIONS TO A USER

(71) Applicant: Amaze PBC, Denver, CO (US)

(72) Inventors: David Mark Silverstein, Longmont, CO (US); Felix Weitzman, Conifer, CO (US)

(73) Assignee: Amaze PBC, Denver, CO (US)

( * ) Notice: Subject to any disclaimer, the term of this patent is extended or adjusted under 35 U.S.C. 154(b) by 246 days.

(21) Appl. No.: 16/776,454

(22) Filed: Jan. 29, 2020

(65) Prior Publication Data

US 2021/0233655 A1    Jul. 29, 2021

(51) Int. Cl.
*G16H 40/67* (2018.01)
*G16H 40/20* (2018.01)

(52) U.S. Cl.
CPC ............ *G16H 40/67* (2018.01); *G16H 40/20* (2018.01)

(58) Field of Classification Search
CPC ........ G16H 40/20; G16H 40/40; G16H 40/67; G16H 10/60; G16H 40/00; G16H 10/00; H04W 4/021; G06Q 10/109; G06Q 10/1095; G06Q 10/10
See application file for complete search history.

(56) References Cited

U.S. PATENT DOCUMENTS

| | | | |
|---|---|---|---|
| 7,925,519 B2 | 4/2011 | Greene et al. | |
| 8,010,717 B2 | 8/2011 | Evans et al. | |
| 8,504,386 B2 | 8/2013 | Manning et al. | |
| 8,554,195 B2 | 10/2013 | Rao | |
| 8,600,008 B2 | 12/2013 | Kraus et al. | |
| 8,924,238 B1 | 12/2014 | Niddy et al. | |
| 9,886,547 B2 | 2/2018 | Baniameri et al. | |
| 9,924,315 B1 | 3/2018 | Cornwall et al. | |
| 10,178,537 B2 | 1/2019 | Rauner | |
| 10,492,023 B1 | 11/2019 | Gurin | |

(Continued)

OTHER PUBLICATIONS

S. R. Dutta and M. Roy, "Providing context-aware healthcare services using circular geofencing technique," 2016 3rd International Conference on Computing for Sustainable Global Development (INDIACom), 2016, pp. 446-451 (Year: 2016).*

(Continued)

*Primary Examiner* — Joseph D Burgess
(74) *Attorney, Agent, or Firm* — Brett A. Schenck

(57) ABSTRACT

A method for providing notifications to a patient associated with a mobile device is provided. The method includes receiving and storing information related to a scheduled visit to the healthcare services facility, determining a first notification based upon the information related to the scheduled visit, and outputting the first notification to the mobile device. The first notification is further based upon the medical history of the patient, the insurance network of the patient, where the patient lives and works, the price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient.

19 Claims, 17 Drawing Sheets

(56) References Cited

U.S. PATENT DOCUMENTS

| | | | |
|---|---|---|---|
| 2014/0100877 A1* | 4/2014 | Rennicks | G06Q 90/20 |
| | | | 705/3 |
| 2015/0032466 A1* | 1/2015 | Vaze | G06Q 50/22 |
| | | | 705/2 |
| 2015/0100326 A1* | 4/2015 | Kowalkiewicz | G06Q 10/06 |
| | | | 705/2 |
| 2016/0253464 A1* | 9/2016 | Balwani | G06Q 10/02 |
| | | | 705/2 |
| 2018/0089387 A1 | 3/2018 | Swank | |
| 2018/0166176 A1 | 6/2018 | Flippen et al. | |
| 2019/0043613 A1 | 2/2019 | Gallagher et al. | |
| 2019/0088106 A1 | 3/2019 | Grundstrom | |
| 2019/0108909 A1* | 4/2019 | Lee | G01C 21/3679 |
| 2019/0237187 A1 | 8/2019 | Carter et al. | |
| 2021/0020307 A1* | 1/2021 | Bhimavarapu | G16H 40/40 |

OTHER PUBLICATIONS

"How geofencing technology complements patient care", Anwer Sadath, Mar. 29, 2016, https://www.linkedin.com/pulse/how-geofencing-technology-complements-patient-care-anwer-sadath (Year: 2016).*

* cited by examiner

SYSTEM AND METHOD FOR PROVIDING NOTIFICATIONS TO A USER

FIELD

This application relates to a system and method for providing notifications to a user.

BACKGROUND

When a patient has a scheduled healthcare related appointment (medical, dental, vision, chiropractic, physical therapy, acupuncture etc.) to a healthcare facility, it would be desirable to conveniently provide the patient relevant information that would make the appointment more productive, pleasant and effective. Also, the type of information may be best provided at certain times before the appointment, or a certain amount of time before the appointment. Further, some patients may have greater capacity to absorb information based on the complexity of the information. Further, some patients may want more information while other patients want less information related to their appointment.

SUMMARY

This application addresses the above-mentioned desires. In one aspect of this application, a computer-implemented method for providing notifications and communication to a patient based on a scheduled visit to a healthcare services facility is provided. The method includes operations performed by at least one computer processor. These operations include a) receiving information related to the scheduled visit to the healthcare services facility, wherein a mobile device is associated with the patient, b) storing the information related to the scheduled visit to the healthcare services facility in a data store, c) determining a first predetermined time in advance of the scheduled visit, d) determining a first notification based upon the information related to the scheduled visit and the first predetermined time in advance of the scheduled visit, wherein the first notification is further based upon one of or any combination of: nothing additional, the medical history of the patient, the insurance network of the patient, where the patient lives or works, the available price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient, f) sending the first notification to or retrieving the first notification from the mobile device when the first predetermined time in advance of the scheduled visit is reached, and g) outputting the first notification to the mobile device when the first predetermined time in advance of the scheduled visit is reached is provided.

In another aspect of this application, a computer-implemented method for providing notifications and communication to a patient based on a first scheduled visit to a healthcare services facility is provided. The method includes operations performed by at least one computer processor. These operations include a) receiving information related to the first scheduled visit to the healthcare services facility, wherein a mobile device is associated with the patient, b) storing the information related to the first scheduled visit to the healthcare services facility in a data store, c) sending a first notification to or retrieving the first notification from the mobile device, wherein the first notification includes information about the first scheduled visit and based upon one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient, d) outputting the first notification to the mobile device, e) determining whether the patient has read the first notification, and f) creating a second notification, wherein the second notification includes information based on determining whether the patient has read the first notification.

Further embodiments of the disclosed a system and method for providing notifications to a user will become apparent from the following detailed description, the accompanying drawings and the appended claims.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

As used herein, the terms "component" and "system" are intended to encompass hardware, software, or a combination of hardware and software. Thus, for example, a system or component may be a process, a process executing on a processor, or a processor. Additionally, a component or system may be localized on a single device or distributed across several devices.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Figure 1:
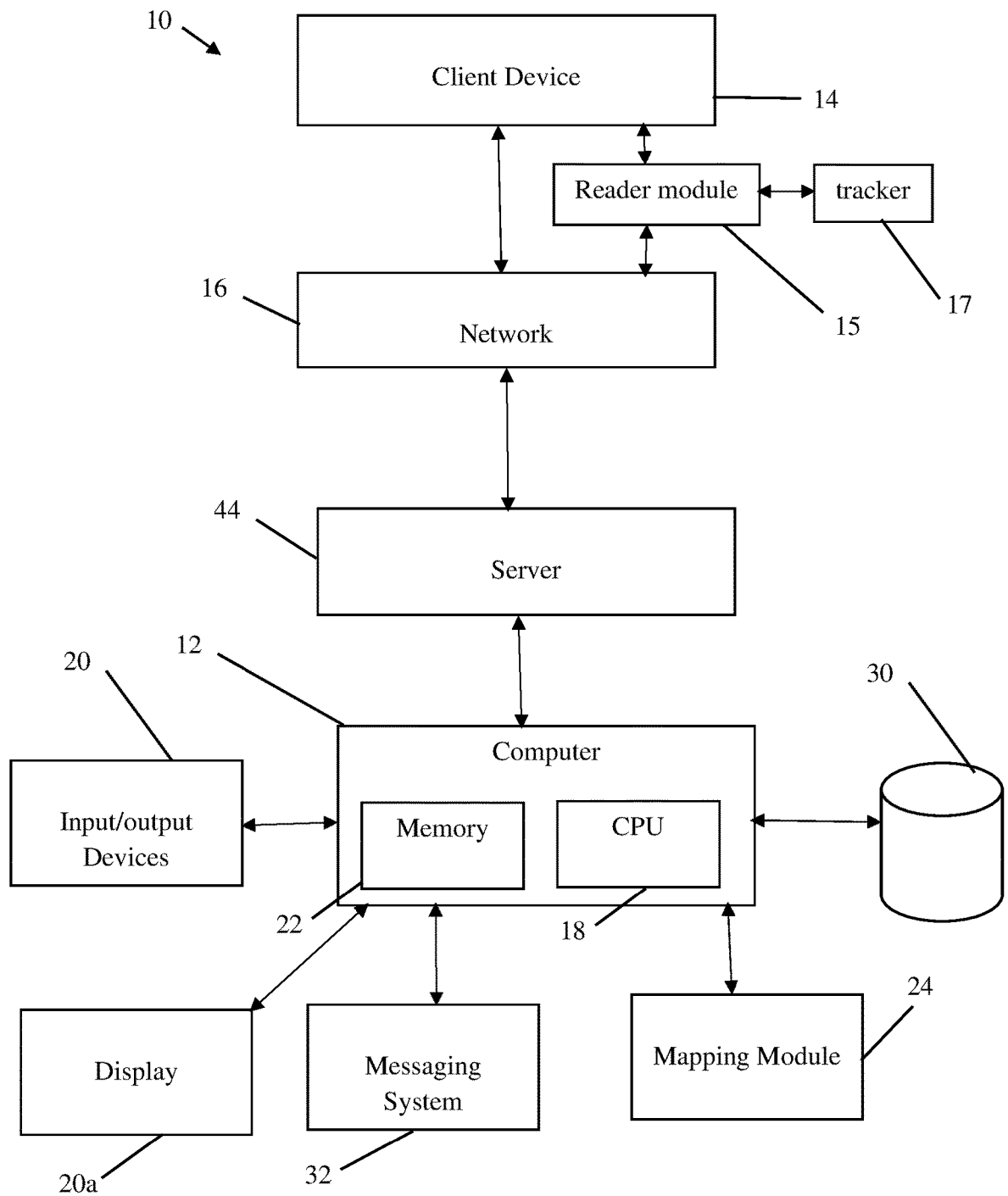
FIG. 1 is a block diagram of the components of the system according to one embodiment of the present invention.

FIG. 1 shows a block diagram of a system 10 that provides notifications to a patient or person as he or she approaches a facility that offers unscheduled healthcare services, or for a scheduled healthcare service according to the present invention. The healthcare services may also be preventative healthcare services. The system 10 may include a computer 12 and a client device 14 such as a mobile device. The components may each be connected and placed in communication with one another over a computer network 16. Embodiments of the network 16 may be constructed using wired or wireless connections between each hardware component connected to the network 16.

The computer 12 may generally comprise a processor 18, otherwise referred to as a central processing unit (CPU), input/output devices 20 such as a display 20a, keyboard, printer etc. coupled to the processor 18, and memory device 22. The processor 18 may perform computations and control the functions of the computer 12, including executing instructions included in the computer code for tools and programs for creating geofenced areas and triggering a geofence notification, in the manner prescribed by the embodiments of the disclosure using the components, wherein the instructions of the computer code may be executed by the processor 18 via memory device 22. The computer code may include software or program instructions that may implement one or more algorithms for implementing the methods for providing a geofence notification. The processor 18 executes the computer code. The processor 18 may include a single processing unit, or may be distributed across one or more processing units in one or more locations (e.g., on a client and server).

The memory device 22 may include input data. The input data includes any inputs required by the computer code. The display 20a displays output from the computer code. The memory device 22 may be used as a computer usable storage medium (or program storage device) having a computer readable program embodied therein and/or having other data stored therein, wherein the computer readable program comprises the computer. The computer 12 may be accessed by a medical professional such as a doctor, physician assistant, nurse practitioner, or other medically or non-medically trained service provider who may provide information, service or support to the patient.

The system may include a notification reader module 15 that determines if the message has been read. The term "module" may refer to a hardware based module, software based module or a module may be a combination of hardware and software resources. A module (whether hardware, software, or a combination thereof) may be designed to implement or execute one or more particular functions, tasks or routines of the system. Embodiments of hardware based modules may include self-contained components such as chipsets, specialized circuitry and one or more memory devices. A software-based module may be part of a program code or linked to program code containing specific programmed instructions loaded in a memory device.

The notification reader module 15 may include a notification tracking device 17. The notification tracking may be accomplished using standard web tracking devices known as cookies and web beacons. For example, when a graphical HTML notification message is sent or retrieved by the mobile device 14, the system may embed an invisible tracking image in the message. The tracking image may be a single-pixel gif or web beacon. The message displayed on the mobile device may be a portion of the message and with a link to display the entire message when a patient touches the link. The link may display the word "more". When a patient touches the link in the message to open the entire message to read, the tracking image is referenced and a tacking code is activated and recorded by the system. The tracking code can also be activating by scrolling the message by sensing clicks or touches on the message to scroll the message to read it. When the system detects a tracking code recorded for a notification, the system will send more information in the message the next time the message is sent or retrieve. If it is not, it will send less information in the message. Reports can be made to show the number of messages that a user touches or clicks on to read the entire message or metrics such as open-rate and click-through rates. Reports can be made on both aggregate response statistics for a group of users and individual response over time The system may include a mapping module 24. The mapping module 24 may create one or more geofenced areas such as one geofenced area 26 (FIG. 6) associated with a healthcare facility or a facility 31 that offers preventative healthcare services based on data in the system. The healthcare facility may also offer healthcare service that can be received on an unscheduled basis. The geofenced area 26 may also be associated with the mobile device 14.

Figure 7:
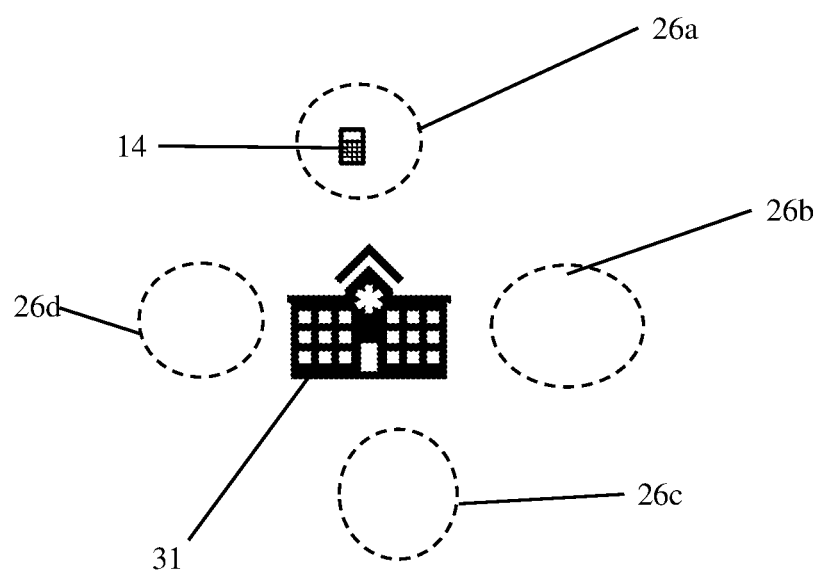
FIG. 7 is a schematic view of a healthcare facility with a first group of geofenced areas associated with a healthcare facility and illustrating a mobile device located within one of the geofenced areas according to the present invention.

The mapping module 24 may alternatively create a first group of geofenced areas 26a-26d (FIG. 7) based on data in the system. The first group of geofenced areas 26a-26d may be created to correspond to or associate with the facility 31 as shown in FIG. 7 and with the mobile device 14. Each geofenced area of the first group may be entered from directions or ways that differ from each of the other one or more geofenced areas in the first group of geofenced areas 26*a*-26*d*. For example, large supermarket, or a hospital emergency room on a hospital campus may have several geofenced areas associated with it, since one large geofenced area encircling the emergency room would not work, because there may be too many false triggers for people going to the hospital for other purposes. Further, there may be cases where there are one or more parking lots, driveways or entrances that are exclusively for the emergency room, so these parking lots and other such location would be associated with a geofenced area for the emergency room. This would also allow for an earlier detection and notification compared with just having a small geofenced area around the emergency room.

In another example, a large supermarket campus may have several geofenced areas associated with it, since one large geofenced area encircling the location providing the healthcare services room would not work, because there may be too many false triggers for people going to the supermarket for other purposes. Further, there may be cases where there are one or more parking lots, driveways or entrances that are exclusively for the location providing the healthcare services, so these parking lots and other such location would be associated with a geofenced area. Additionally, the geofenced area, which may be defined by other location services such as wifi hotspots or beacons, may be inside a building versus outside. For example, the geofenced area could be a particular store or clinic inside a shopping mall or a clinic inside of a department store.

The mapping module 24 may receive geofence configuration data defining the properties of each geofenced area. The geofence configuration data may include data defining each geofences' name, location, and size or virtual boundary limits (i.e. longitude, latitude and radius, proximity, or detection of other location determining digital signals). The geofencing configured may comprise a defined geographic boundary area (a radius around an address, geo position coordinates, or other specified location or a geometric boundary such as a geofence or a proximity (distance) from a specific location.

The mapping module 24 may create interruption conditions based on data in the system 10 to prevent outputting messages to the client device 14 when the location data of the client device 14 is determined to be within a geofenced area. Other components in the system may create the interruption conditions as well. This avoids unnecessary triggers. One interruption conditions may include prior to outputting the notification to the mobile device, determining if the patient had the at least one healthcare service within a predetermined time ago and preventing the outputting of the notification upon determining that the patient had the at least one healthcare service within a predetermined time ago. Another interruption condition may include prior to outputting the notification to the mobile device, determining that the at least one healthcare service should not be provided to the patient and preventing the outputting of the notification upon determining that the at least one healthcare service should not be provided to the patient. Determining that the at least one healthcare service should not be provided to the patient may be based on the medical history of the patient. Determining that the at least one healthcare service should not be provided to the patient may also be based on one or more insurance claims of the patient.

Another interruption condition may include prior to outputting the notification to the mobile device, determining that the preference of the patient is to not output the notification and preventing the outputting of the notification upon determining that the preference of the patient is to not output the notification. Another interruption condition may include prior to outputting the notification to the mobile device, determining that the at least one healthcare service is not in the insurance network of the patient and preventing the outputting of the notification upon determining that the at least one healthcare service is not in the insurance network of the patient. Another interruption condition may include prior to outputting the notification to the mobile device, determining that the cost of the at least one healthcare service is not available or more than a predetermined amount at the facility and preventing the outputting of the notification upon determining that the cost of the at least one healthcare service is not available or more than a predetermined amount at the facility. Another interruption condition may include prior to outputting the notification to the mobile device, determining that the quality of the at least one healthcare service at the facility is not adequate and preventing the outputting of the notification upon determining that the quality of the at least one healthcare service at the facility is not adequate. This information may be stored in a data store 30, as well as from location data from his or her client device 14.

Other interruption conditions may be based on information about where a patient or person associated with the client device 14 works, lives, and/or where or when his or her daily activities (e.g. commuting, shopping, walking, running, bike-riding, etc.) are performed. This information may come from his or her addresses (home, work, gym, etc.) stored in a data store 30, as well as from location data from his or her client device 14. For example, an interruption condition may be created for the workplace of a person associated with the client device 14 and activated only during the working hours of the person if the workplace is a healthcare facility. A person may operate the computer 12 to enter the data to create the interruption condition. The interruption conditions may be based on one or more predetermined dates and times when the location data of the mobile device is determined to be within the geofenced area. The interruption conditions may also be based on determining that the patient frequently passes through the geofenced area en route to another location. The interruption conditions may also be based on determining that the patient frequents the geofenced area for purposes unrelated to receiving healthcare services.

The system 10 may include a messaging system 32. The messaging system 32 may perform the functions, tasks and services of the system 10 directed toward creating notifications or messages and notification events associated with the system such as notifications to the client device 14. The message system may send a one or more notifications upon the occurrence of one or more of the programmed transitions. For example, when a client device 14 breaches a virtual boundary of a geofenced area (entering or exiting), a geofence notification may be transmitted to the client device 14.

Figure 2:
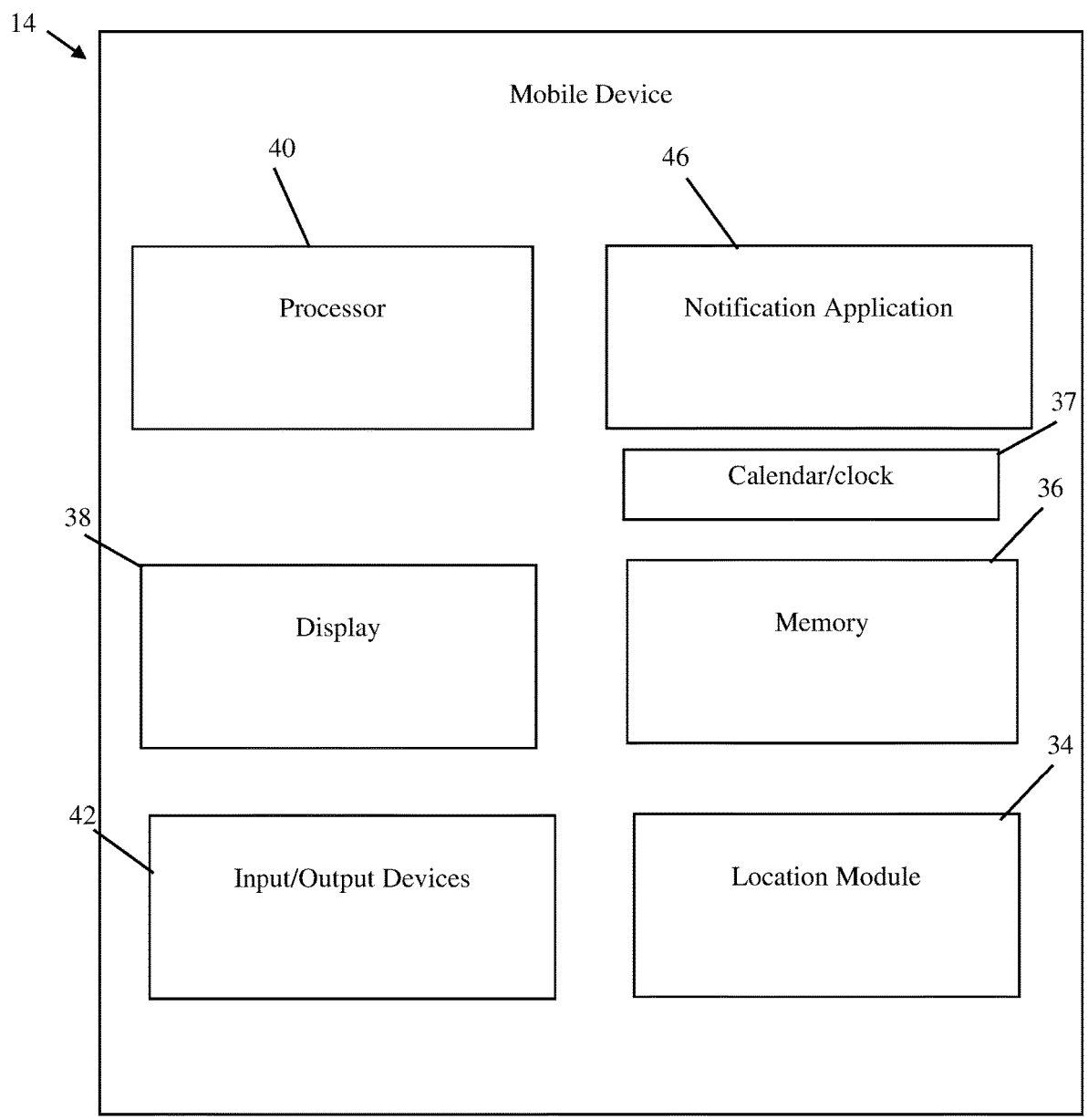
FIG. 2 is a block diagram of the client device and related elements according to the system of FIG. 1.

The system 10 may further comprise a location module 34 associated with the client device 14 as illustrated in FIG. 2. The location module 34 detects, processes and communicates the location of the client device associated with the user. Location sensing technology may include but is limited to global positioning systems (GPS), Wi-Fi, Bluetooth, 3G, 4G, 5G, 6G, 7G cellular technology, near field communications, radio frequency identification (RFID), beacons, and any other location identifying signal. The location module 34 may be comprised of hardware and/or software capable of utilizing a positioning system to pinpoint the current location of the client device 14 and/or previously stored locations of the client device 14 that may be saved in a memory device 36 or data store 30. The location module 34 may include a transmitter, receiver and/or transceiver for receiving location data from a positioning system or broadcasting the location data to the system 10. The location module 34 may save, store and update one or more sets of location data to a memory device onboard the location module 34 or, the location module 34 may store the location information to the memory device 36 or the data store 30. The location module 34 may include any sort of system that informs the mobile device of its geolocation including, but not limited to, the Global Positioning System of satellites circling the Earth.

With continued reference to FIG. 2, the client device 14 may be a portable device such as a mobile device in operative communication with each other. The mobile device 14 may optionally be any computing device small enough to hold and operate in the hand. The mobile device 14 may also be built into a vehicle. The mobile device 14 may comprise a display 38 having a flat or curved screen interface that provides a touchscreen interface with digital buttons and keyboard, and/or physical buttons along with a physical keyboard. The mobile device 14 may be voice activated. The mobile device 14 may connect to the internet and interconnect with other devices such as car entertainment systems or headsets via Wi-Fi, Bluetooth, cellular networks or near field communication (NFC). The flat screen interface may be an LCD flat screen interface, an OLED flatscreen interface, or other suitable type of flat screen interface. Alternatively, the display 38 may being the form of a hologram. The mobile device 14 may be a cell phone, smart phone, smart watch, tablet, PDA, laptop, notebook or other suitable portable or mobile device. The mobile device 14 is configured to detect its location and hence the location of a user using the mobile device 14 or other person near the mobile device 14.

The mobile device 14 includes one or more processors 40 and the memory device 36. The memory device 36 may contain a user identification module that may in turn contain a user identifier and/or user information. The user identifier may be a unique number or code that uniquely identifies the user of the mobile device. The mobile device 14 may also include input/output devices 42 such as a camera capable of taking still or video pictures and have the capability to make video calls (see FIG. 5). An antenna in the mobile device may send and receive wireless signals from sources such as the radio antenna and satellite. The antenna may, in some implementations, communicate directly with the server such as by exchanging wireless signals. The mobile device 14 may further comprise other input/output devices 42, such as a microphone and a speaker used, for example, in an implementation in which the mobile device 14 functions as a telephone. In some implementations, the mobile device 14 may also include a calendar/clock 37 and a network interface. The calendar/clock 37 may calculate time, date, and other data that can be derived from time data and date data. This time and date data may be based on GPS signals continually received by the mobile device. The message system 32 may receive the time and date data from the calendar/clock 37 to determine when to send messages and what type message or notification to send.

For example, the message system may send a first notification based upon the information related to a scheduled visit to the healthcare facility and a first predetermined time in advance of the scheduled visit. The first notification may be further based upon one of or any combination of the medical history of the patient, the insurance network of the patient, where the patient lives and works, the price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient. The first notification may include information that is related to the first predetermined time in advance of the scheduled visit. For example, if the first predetermined time is more than 2 months in advance of the schedule visit, the first notification message may include reminders of what you need to do before the visit such as to not to eat for 12 hours before your scheduled visit.

The message system may send a second notification based upon the information related to a scheduled visit to the healthcare facility and a second predetermined time in advance of the scheduled visit. Additional subsequent notifications may be sent also based upon the information related to a scheduled visit to the healthcare facility and a second predetermined time in advance of the scheduled visit. The second notification or additional notifications may be further based upon one of or any combination of the medical history of the patient, the insurance network of the patient, where the patient lives and works, the price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient. The second notification may include information that is related to the first predetermined time in advance of the scheduled visit. For example, if the second predetermined time is 3 weeks in advanced of the scheduled visit, the second notification may provide information about reading material related to your medical condition. For example, if the patient has an appointment with an orthopedic surgeon for back pain, the notification might include an article that explains why experts believe 70% of back surgeries are unnecessary, or what back surgery might be premature if you've tried certain alternative treatments for back pain.

Other notifications may include information that will make the appointment more productive, pleasant, and/or effective. The notification further includes an invitation or suggestion or option to initiate a video or audio call or text chat to a qualified person that can help the patient regarding the scheduled visit to the healthcare facility. The notification may include the preference of the patient for having a particular healthcare service related to the scheduled visit performed at a certain time. The notification may include a list of facilities that perform the particular healthcare service that the patient scheduled.

The mobile device 14 includes applications that manage interactions between a server 44 (FIG. 1) and the mobile device 14. The applications may include a notification application 46. The data store 30 associated with the system 10 may contain data on healthcare facilities and their type. For example, the type of healthcare facility stored in the data store 30 may be a hospital, free-standing emergency, urgent care, or walk-in clinic. One or more of the healthcare facilities stored in the data store 30 may be associated with the patient associated with the mobile device 14. For example, the healthcare facility may be in the patient's insurance network with this data stored in the data store 30.

The data store 30 may also store personal and medical information about the patient in the form of a record. This and other information may be made available to the patient or other person via the mobile device 14 or computer 12. The data store 30 may store an address associated with a property and a geofenced area associated with the property. The data store 30 also may store all the mobile phone numbers of the smartphones which have the notification application 46 installed. The installed notification application 46 has the geofence information so that the mobile device 14 knows, using GPS technology, whether it is inside or outside the geofenced area.

The data store 30 may store information on patient(s) or person(s) associated with the mobile device related to their medical history to speed the process of receiving the services of the healthcare facility, lists of medical questions to ask, ratings on the facility being entered or the medical professionals practicing at that facility, information about whether the facility and\or medical providers participate in their insurance network, the medical providers practicing at the healthcare facility, wait times at the healthcare facility, and the proximity to other healthcare facilities and information about the prices of the facility or providers. This data may be displayed on the display 38 of the mobile device 14. The data store 30 may store the interruption conditions for preventing the outputting of the notification when the location data of the mobile device is determined to be within the geofenced area that are created using the mapping module 24 in exemplary embodiments.

The data store 30 may store information on the medical history of the patient, the insurance network of the patient, where the patient lives and works, the price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient.

The data store 30 may store information as to where in the facility that the at least one healthcare service is offered that can be received on an unscheduled basis, whether or not the healthcare service is covered by the patient's insurance, the cost of the healthcare service, the out-of-pocket cost by the patient of the healthcare service, and when the patient should not receive the healthcare service for other medical reasons. The data store may store information as to when a particular healthcare service is due for the patient. For example, the data store may store information as to when the patient's blood pressure should be tested, when an eye examination should be performed on the patient, and when lab work for the patient's physical examination is due. The data store may also store information as to whether the facility 31 offers the particular healthcare service such as lab work, blood pressure testing, and eye examination.

Figure 4:
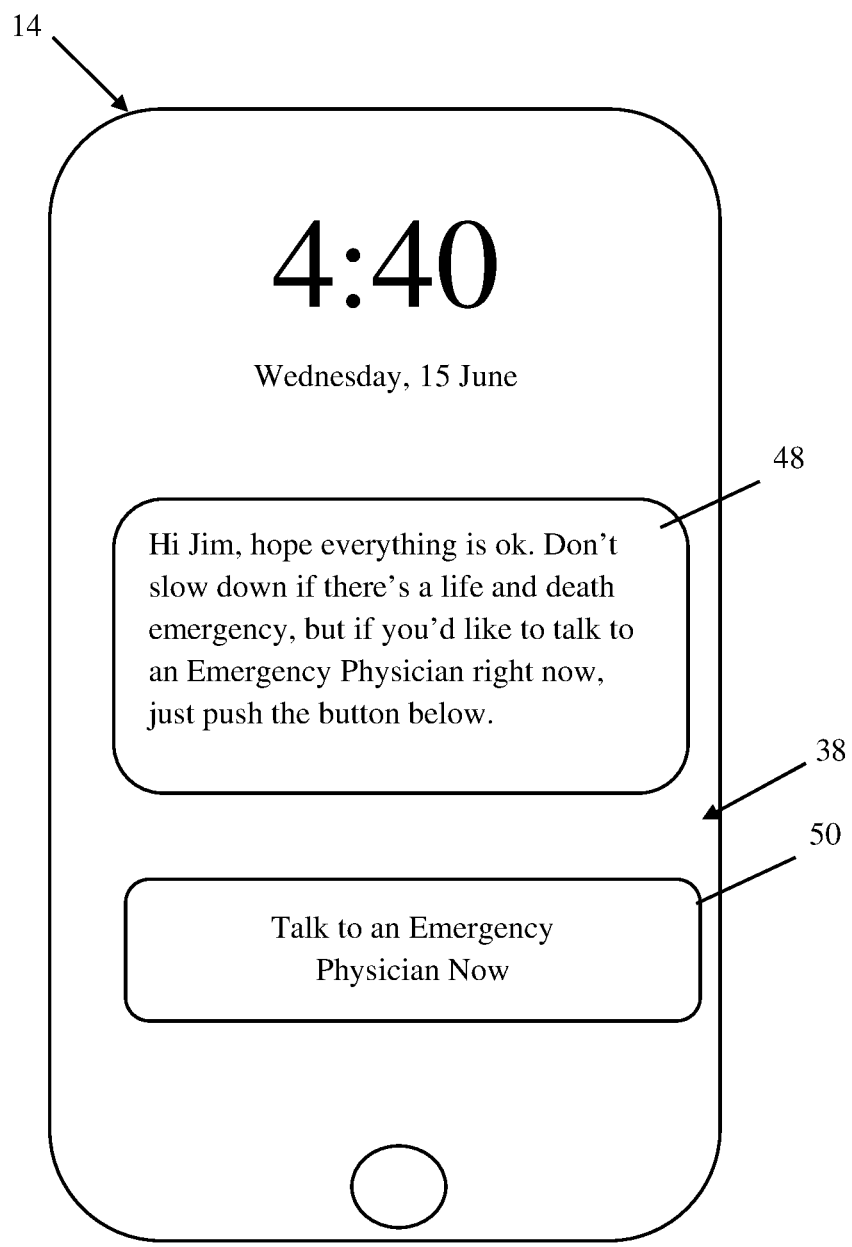
FIG. 4 is a schematic front view of mobile device displaying a message and message button on the display of the mobile device of the system according to FIG. 1.

The system 10 may identify a type of healthcare facility and then map or link that type with a certain message. The message may include a button. For example, an emergency healthcare facility may be linked with a notification or message 48 and a message button 50 for making video calls displayed on the display 38 of the mobile device 14 as shown in FIG. 4. The computer 12 may display on its display 20*a* the above-mentioned information corresponding to the healthcare facilities or the patient associated with the client device or other information for the medical professional to access.

The computer 12 and mobile device 14 may communicate with the server 44 via the internet over the network 16 as illustrated in FIG. 1. The network may include any one or combination of multiple different types of networks, such as cable networks, local area networks, personal area networks, wide area networks, the Internet, wireless networks, ad hoc networks, mesh networks, and/or the like. In some implementations the satellite and/or the radio antenna may provide network connectivity to the mobile device as well as provide geolocation. For example, the radio antenna may provide network access to the mobile device according to the International Mobile Telecommunications-2000 standards (3G network) or the International Mobile Telecommunications Advanced standards (4G network) or the 5G or 6G networks. Other implementations may include one source of geolocation data such as the satellite and a separate source of network connectivity such as a Wi-Fi hotspot. The server may house or otherwise have a connection to multiple data stores including user information and/or other data stores. The server 44 and data stores can be stored where desired, for example in a cloud.

Generally, the user information contains information about the user associated with the mobile device 14. The notification application 46 is operatively connected to the server 44 which is connected to the data store 30. The notification application 46 has notifications and messages associated with different types of conditions. The messages may include buttons for the user to operate. For example, FIG. 4 shows a notification message 48 and message button 50 for making video calls generated by the messaging system 32 when the mobile device 14 enters a geofenced area associated with a free-standing emergency facility. The notifications or messages may be stored in the memory 36 of the mobile device 14 or in the data store 30. One or more notifications may include information about one of or any combination of: that the location offers at least one healthcare service that can be received on an unscheduled basis, where in the facility that the at least one healthcare service is offered, whether or not the healthcare service is covered by the patient's insurance, the cost of the healthcare service, the out-of-pocket cost by the patient of the healthcare service, wait time at the facility for the healthcare service, and when the patient should not receive the healthcare service for other medical reasons. This notification may be outputted to the mobile device and displayed on the display when the location data of the mobile device is determined to be within the geofenced area that corresponds to the preventative healthcare facility. Alternatively, or in addition, the notification may include a voice message that may include the above-mentioned information.

Figure 8:
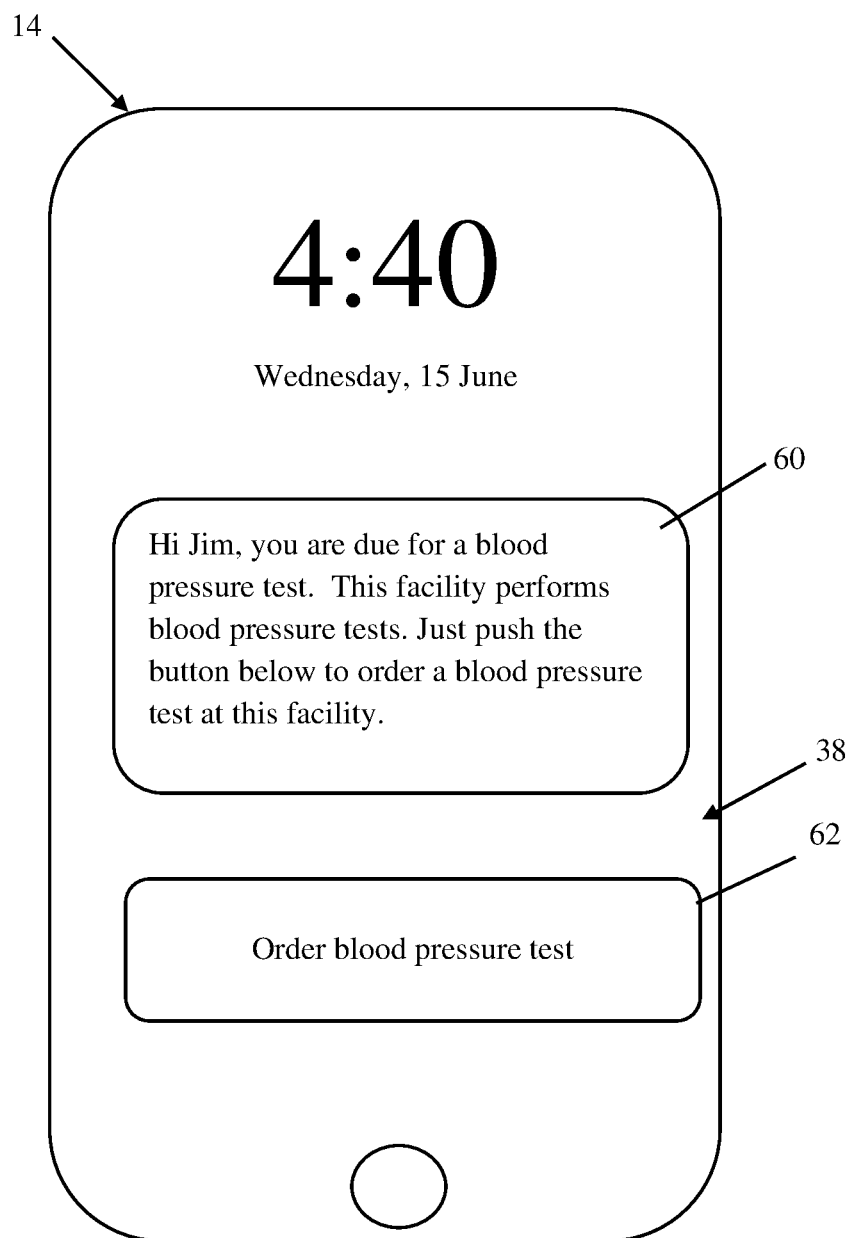
FIG. 8 is a schematic front view of mobile device displaying another message and message button on the display of the mobile device of the system according to FIG. 1.
Figure 9:
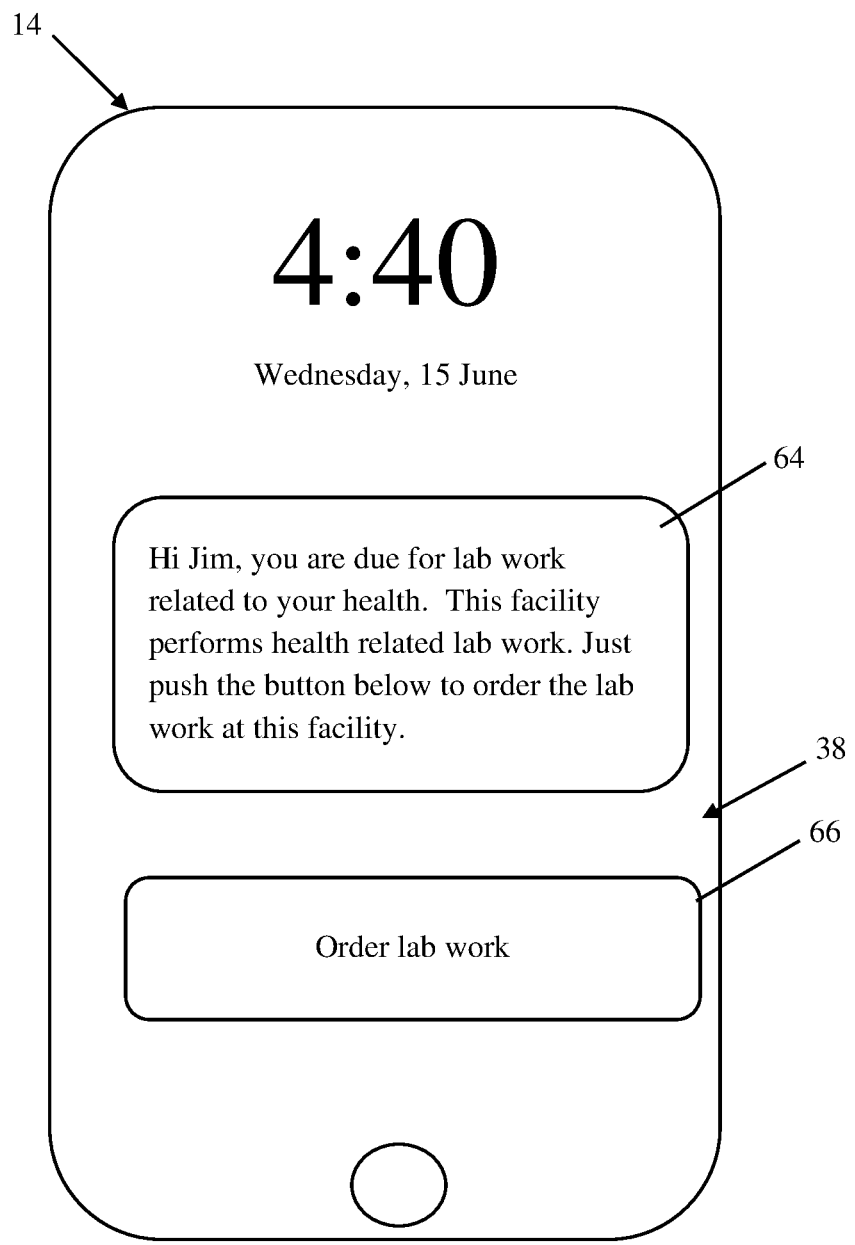
FIG. 9 is a schematic front view of mobile device displaying another message and message button on the display of the mobile device of the system according to FIG. 1.
Figure 10:
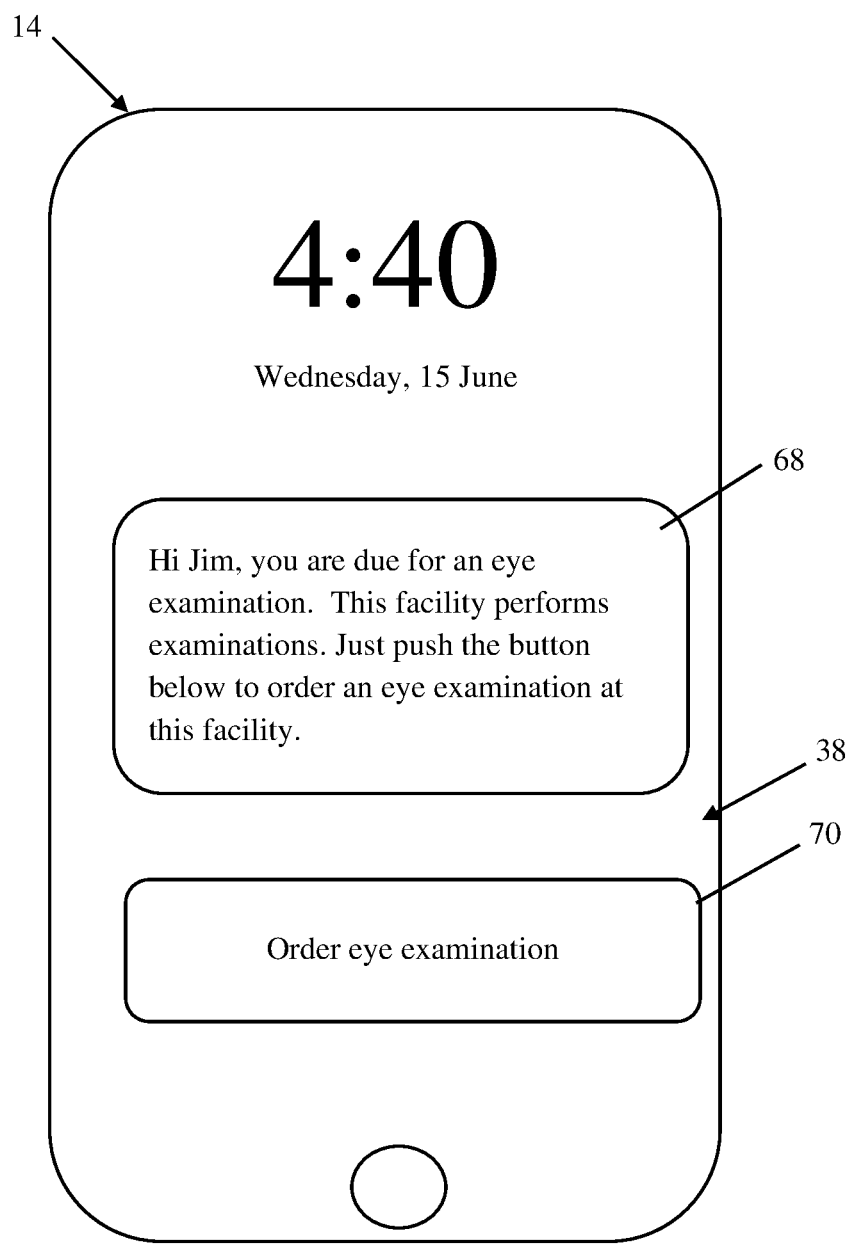
FIG. 10 is a schematic front view of mobile device displaying another message and message button on the display of the mobile device of the system according to FIG. 1.

The notification may include a message that the particular healthcare service is due for the patient and also prompt the patient to place an order for the particular healthcare service as show in FIGS. 8-10. For example, the message 60 may be that the healthcare service is providing blood pressure testing and also prompt the patient to request or place an order for the patient to have his or her blood pressure tested at the facility 31 by pressing a button 62 as shown in FIG. 8. The message 64 may be that the healthcare service may be providing lab work for the patient's physical examination and also prompt the patient to request or place an order for the lab work by pressing a button 66 as shown in FIG. 9. The message 68 may be that the healthcare service is providing eye examinations and also prompt the patient to request or place an order for the patient to have his or her eye examined at the facility 31 by pressing a button 70 as shown in FIG. 10. This notification may be outputted to the mobile device 14 and displayed on the display 38 when the location data of the mobile device is determined to be within the geofenced area that corresponds to the preventative healthcare facility 31. Alternatively, or in addition, the notification may include a voice message that may include the above-mentioned information.

Figure 3:
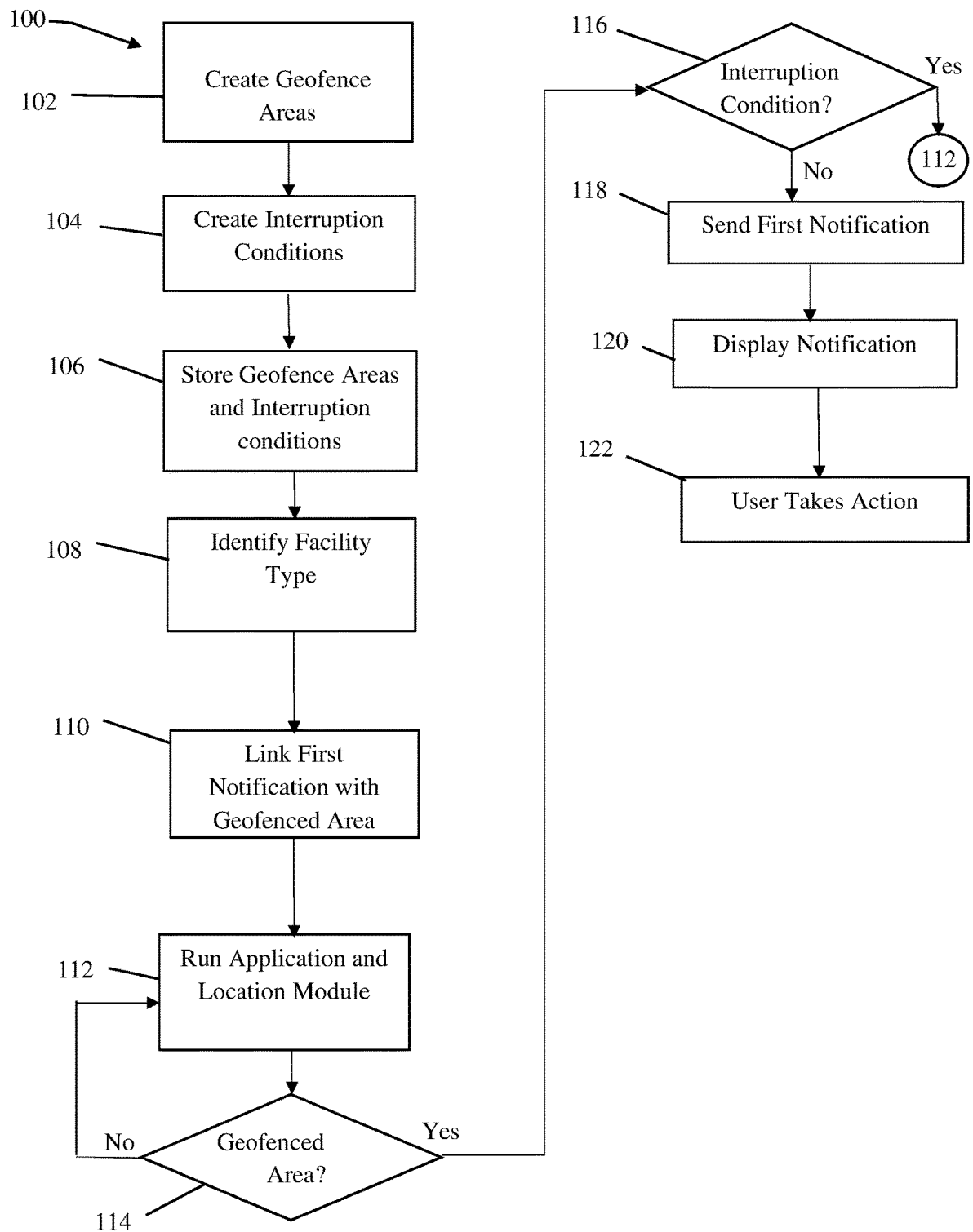
FIG. 3 is a flow diagram of an exemplary method according to FIG. 1.

With reference now to FIG. 3, an example methodology 100 is illustrated and described. While the methodology is described as being a series of acts or steps that are performed in a sequence, it is to be understood that the methodology is not limited by the order of the sequence. For instance, some acts or steps may occur in a different order than what is described herein. In addition, a step may occur concurrently with another step. Furthermore, in some instances, not all steps may be required to implement a methodology described herein.

Moreover, the steps or acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodology may be stored in a computer-readable medium, displayed on the display device, and/or the like.

Figure 6:
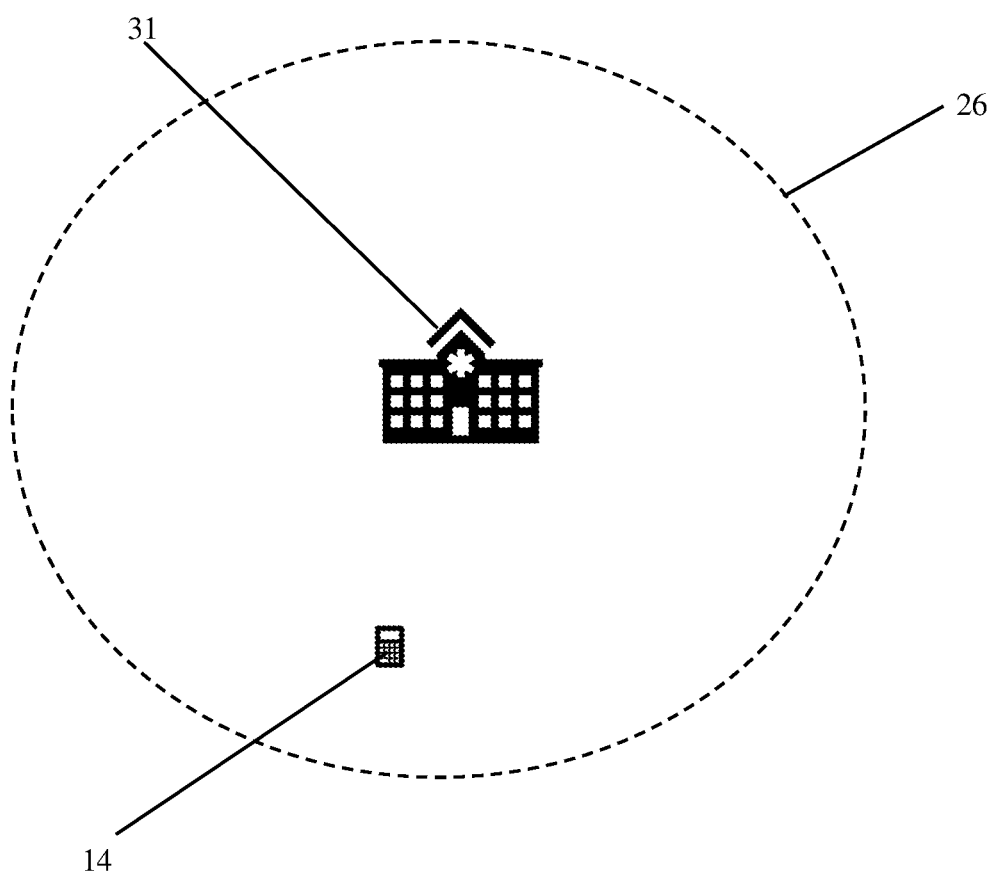
FIG. 6 is a schematic view of a healthcare facility surrounded by a geofence area associated with a healthcare facility and illustrating a mobile device located within the geofenced area according to the present invention.

In each step of this sequence of client-server message exchanges, a computer may process a request and return data. In step 102, the geofenced areas are created using the mapping module 24 based on data in the data store 30. One or more of the geofenced areas created may correspond to or be associated with the mobile device 14 associated with the patient and a location that has the facility 31. The facility 31 may offer one or more preventative healthcare services or one or more healthcare services. For example, one geofenced area 26 may be created for the facility 31 as shown in FIG. 6. In another example, a first group of geofenced areas 26a-26d may be created to correspond to the facility 31 as shown in FIG. 7. For example, a location such as an emergency room or an area that screens for cancer on a hospital campus may have several geofenced areas, since one large geofenced area encircling that location would not work, because there may be too many false triggers for people going to the hospital for other purposes. Further, there may be cases where there are one or more parking lots, driveways or entrances that are exclusively for that location, so these parking lots and other such locations would be associated with a geofenced area for that location.

In step 104, the interruption conditions for preventing the outputting of the notification when the location data of the mobile device is determined to be within the geofenced area may be created using the mapping module 24. In step 106, the geofenced areas and any interruption conditions are stored in the data store. In step 108, the facility may be identified. For example, the facility 31 stored may be identified as a hospital, free-standing emergency, urgent care, or walk-in clinic and other information related to that facility. In step 110, a first predetermined notification stored in the data store 30 or in the memory of the mobile device 14 may be linked with the one or more geofenced areas of the facility 31. This notification may include messages with information about one of or any combination of: that the location offers at least one healthcare service that can be received on an unscheduled basis, where in the facility that the at least one healthcare service is offered, whether or not the healthcare service is covered by the patient's insurance, the cost of the healthcare service, the out-of-pocket cost by the patient of the healthcare service, wait time at the facility for the healthcare service, and when the patient should not receive the healthcare service for other medical reasons.

Alternatively or in addition, the notification may include a message that the particular healthcare service is due for the patient and also prompt the patient to place an order for the particular healthcare service. For example, the healthcare service may be providing lab work for the patient's physical examination. The healthcare service may be testing the blood pressure of the patient. The healthcare service may be providing an eye examination of the patient. This notification may be outputted to the mobile device and displayed on the display when the location data of the mobile device is determined to be within the geofenced area that corresponds to the preventative healthcare facility. The notification may further include an invitation or suggestion to initiate a video or audio call to a qualified person that can help the patient regarding the situation.

In step 112, the mobile device 14 is turned on with the notification application 46 launched and running and the location module 34 running so that the system 10 receives location data of the mobile device 14. In step 114 the notification application 46 determines when the mobile device 14 is located within a geofenced area associated with the facility 31 stored in the data store 30. This may occur during an unscheduled visit to the healthcare facility by the patient. If the mobile device 14 is located within the geofenced area, then the system 10 may check in step 116 whether there is an interruption condition for that geofenced area. If there is an interruption condition, no notification is outputted to the mobile device 14 and the method goes back to step 112 to continue to receive location data of the mobile device 14.

If the mobile device 14 is located within the geofenced area and there is no interruption condition, then in step 118, the messaging system 32 sends the first predetermined notification to the mobile device 14 or the predetermined notification is retrieved from the memory of the mobile device 14. In step 120, the notification is displayed on the display 38 of the mobile device 14. The notification may include a message button 50 to give the option to place an audio or video call with a qualified healthcare professional an invitation or suggestion to initiate a video or audio call to a qualified person that can help the patient regarding the unscheduled visit. The message may also prompt the patient to request or place an order for the particular healthcare service. Alternatively or in addition, other ways to output the message may be provided such as an audio message outputted through the speakers of the mobile device. In step 122, the user may take action based on the displayed message(s).

Figure 5:
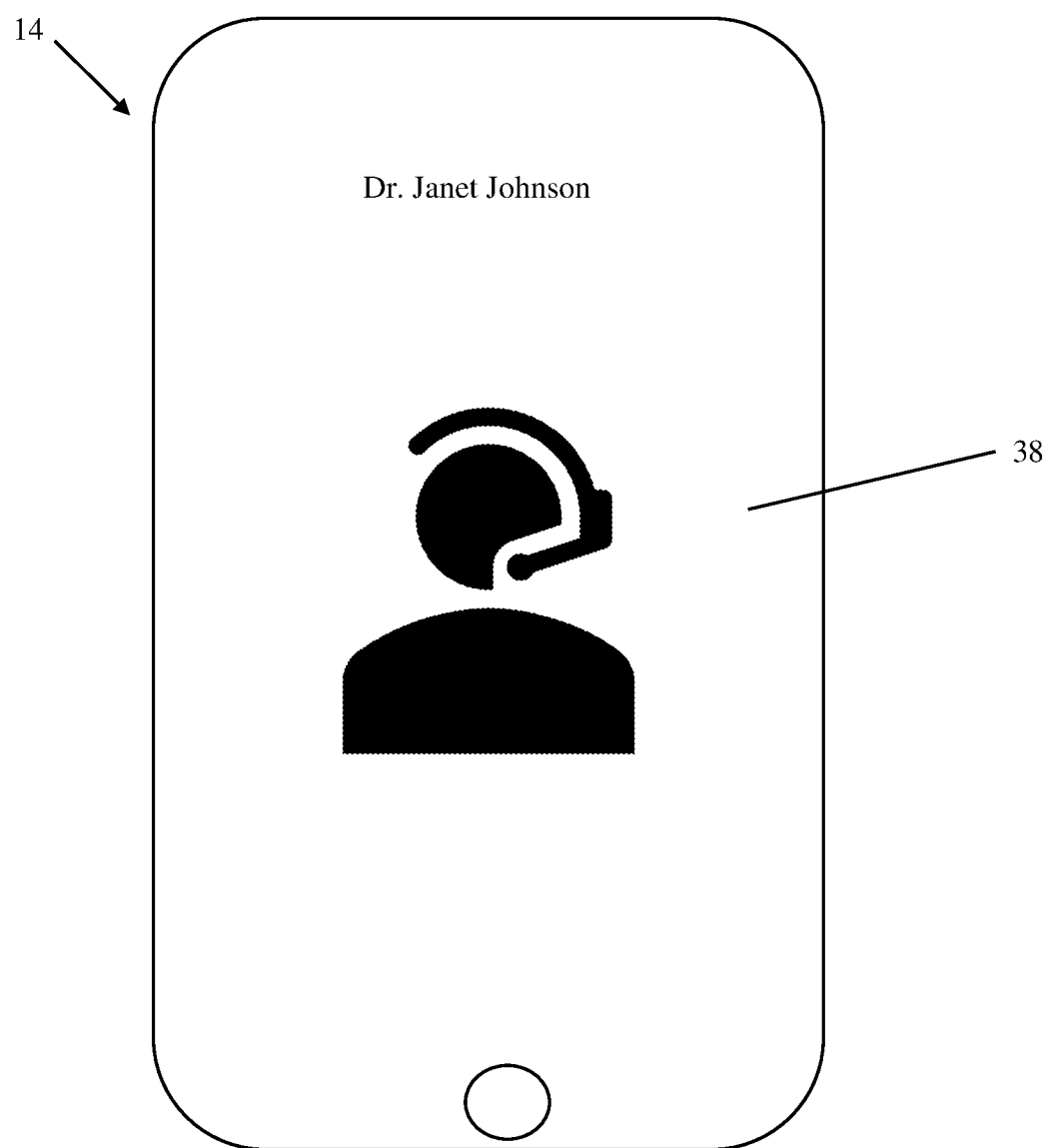
FIG. 5 is a schematic front view of mobile device displaying an image of a video call initiated by the user on the mobile device of the system according to FIG. 1.

For example, FIGS. 8-10 shows a message that a particular type of healthcare service is due and prompts the patient to order the healthcare service. In FIG. 8, the message 60 notifies the patient that their blood pressure test is due and that this particular facility 31 performs blood pressure tests. The message 60 also prompts the patient to order the blood pressure test and displays a button 62 that the patient can press to order the blood pressure test at the facility 31. In FIG. 9, the message 64 notifies the patient that lab work related to their health is due and that this particular facility 31 performs health related lab work. The message 64 also prompts the patient to order the blood pressure test and displays a button 66 that the patient can press to order that their lab work be performed for them at the facility 31. In FIG. 10, the message 68 notifies the patient that their eye examination is due and that this particular facility 31 performs eye examinations. The message 68 also prompts the patient to order the eye examination and displays a button 70 that the patient can press to order the eye examination at the facility 31. The message may also have a button to place a video or audio call to a doctor or other qualified professional that can help the patient regarding the visit as illustrated in FIG. 5. The method may also include enabling the user to cancel the notification without placing the call or taking further action.

FIG. 4 shows another example of a notification message and a message button generated by the messaging system 32 when the mobile device 14 enters the first geofenced area 26a associated with a free-standing emergency facility. If the user presses the message button 50 on the display 38, a video call will be placed with a doctor or other qualified professional that can help the patient regarding the unscheduled visit as illustrated in FIG. 5. The medical professional may be a doctor, physician assistant, nurse practitioner, or other medically or non-medically trained service provider who may provide information, service or support to the patient and can help the patient regarding the unscheduled visit. The method may also include enabling the user to cancel the notification without placing the call or taking further action.

In one example, a video call may be placed with a doctor to determine whether or not the injury requires going to an emergency medical facility. For certain injuries, the doctor may ask the patient to take a photograph of the injury using the mobile device and send the photograph to the doctor by email, text, or other suitable mode. Upon analyzing the photograph, the doctor may determine that the injury does not require the services of an emergency healthcare facility. The doctor may operate the computer to search the data store 30 and find an urgent care facility near the patient's location based on the mobile phone location and then suggest to the patient to go to the less costly urgent care facility, since the injury does not require use of an emergency healthcare facility.

Figure 11A:
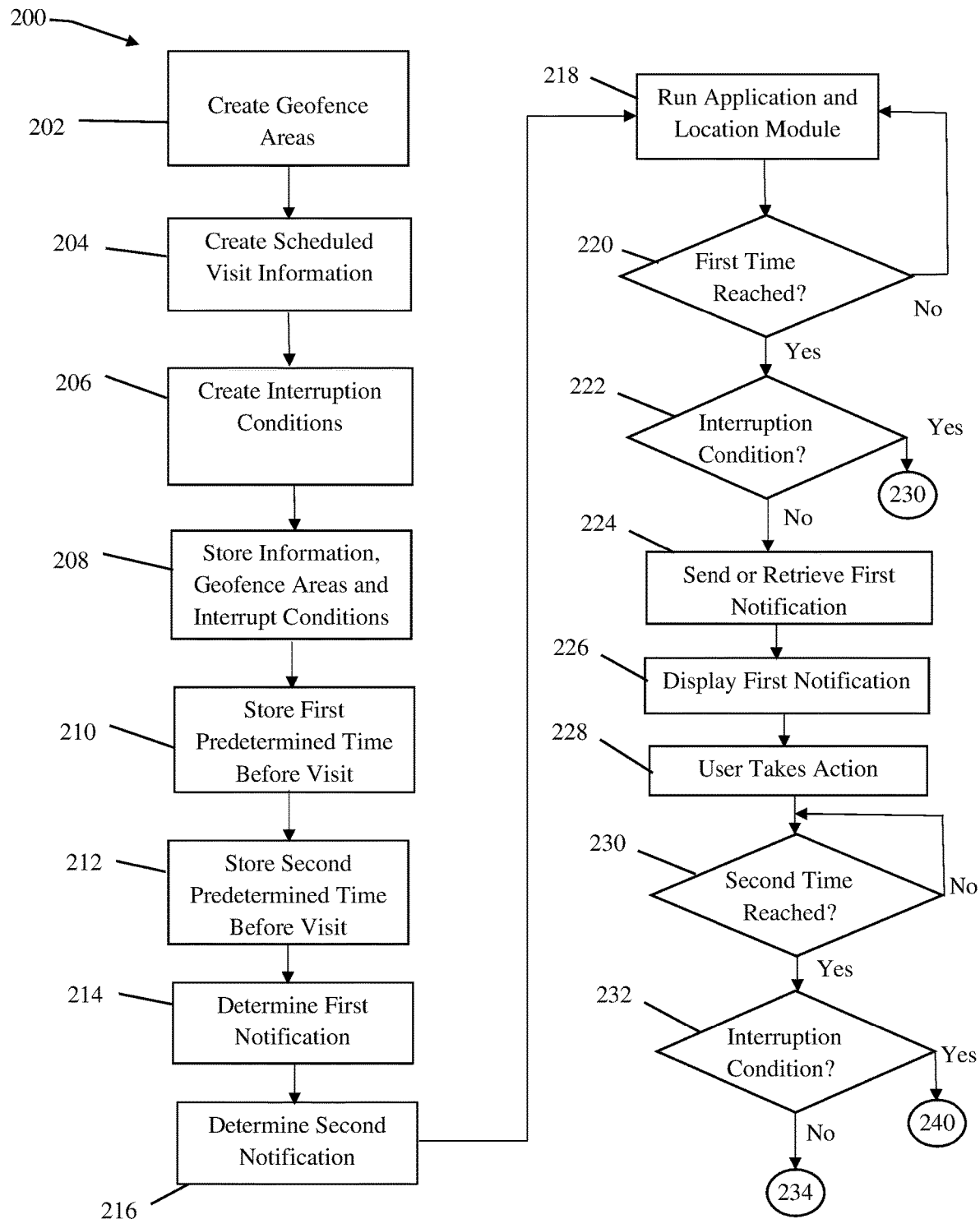
FIGS. 11A and 11B are in combination a flow diagram of another exemplary method according to FIG. 1.
Figure 11B:
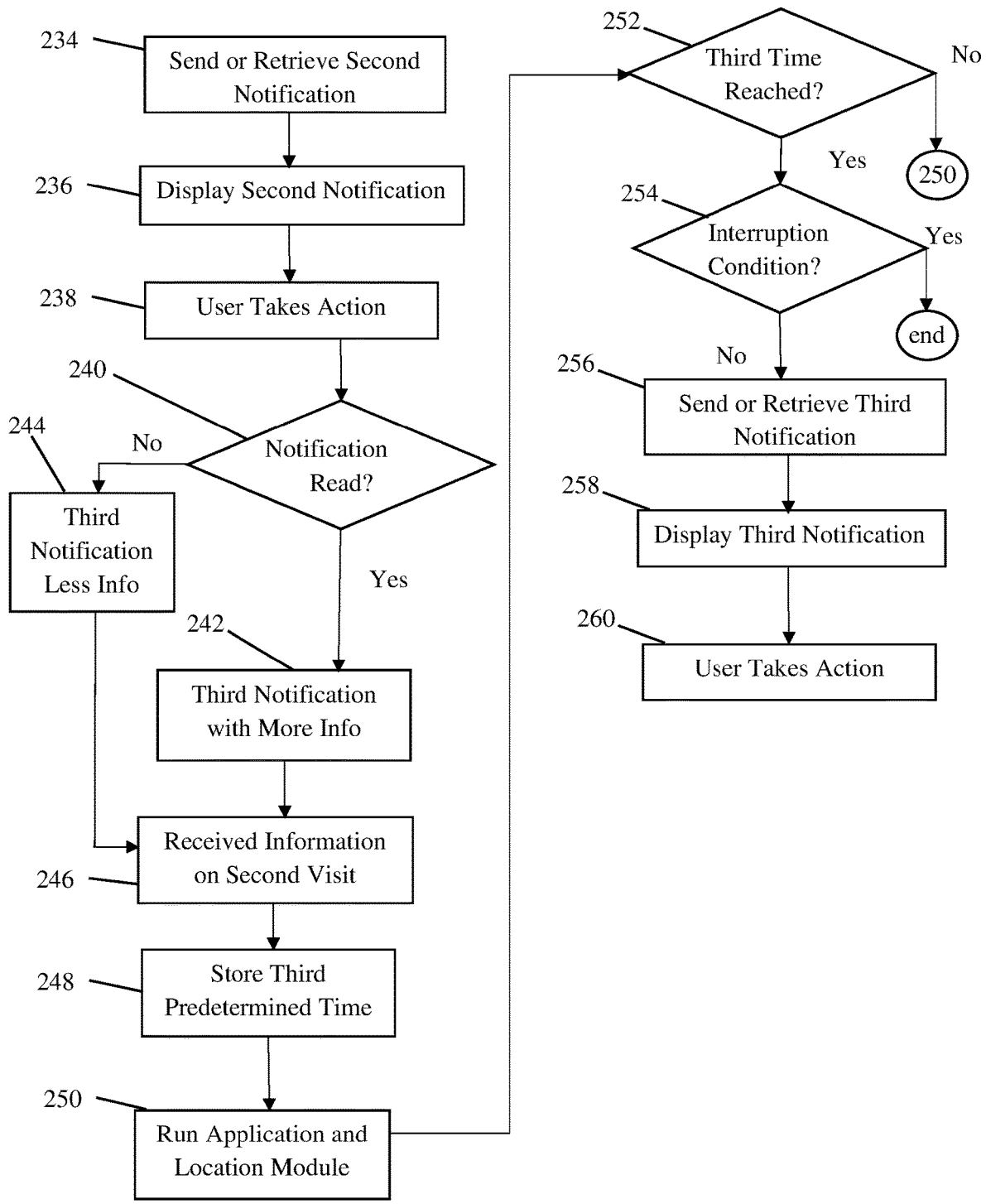

With reference now to FIGS. 11A and 11B, an example methodology 200 is illustrated and described. While the methodology is described as being a series of acts or steps that are performed in a sequence, it is to be understood that the methodology is not limited by the order of the sequence. For instance, some acts or steps may occur in a different order than what is described herein. In addition, a step may occur concurrently with another step. Furthermore, in some instances, not all steps may be required to implement a methodology described herein.

Moreover, the steps or acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodology may be stored in a computer-readable medium, displayed on the display device, and/or the like.

In each step of this sequence of client-server message exchanges, a computer may process a request and return data. In step 202, the geofenced areas are created using the mapping module 24 based on data in the data store 30. One or more of the geofenced areas created may correspond to or be associated with the mobile device 14 associated with the patient and a location that has the facility 31. The facility 31 may offer one or more healthcare services. For example, one geofenced area 26 may be created for the facility 31 as shown in FIG. 6. In another example, a first group of geofenced areas 26a-26d may be created to correspond to the facility 31 as shown in FIG. 7. For example, a location such as an emergency room or an area that screens for cancer on a hospital campus may have several geofenced areas, since one large geofenced area encircling that location would not work, because there may be too many false triggers for people going to the hospital for other purposes. Further, there may be cases where there are one or more parking lots, driveways or entrances that are exclusively for that location, so these parking lots and other such locations would be associated with a geofenced area for that location.

In step 204, information related to a scheduled visit to the healthcare facility 31 by the patient associated with the mobile device 14 is created. In step 206, the interruption conditions for preventing the outputting of the notification may be created. In one example, the interruption conditions for preventing the outputting of the notification may be based on when the location data of the mobile device 14 is determined to be within the geofenced area using the mapping module 24. In step 208, the information related to the scheduled visit to the healthcare services facility 31 by the patient associated with the mobile device 14, the geofenced areas, and any interruption conditions are stored in the data store 30. In step 210, a first predetermined time in advance of the scheduled visit is determined and stored in the data store 30. In step 212, a second predetermined time in advance of the scheduled visit is determined and stored in the data store 30. The second predetermined time may be less than the first predetermined time.

In step 214, a first notification is determined based upon the information related to the scheduled visit and the first predetermined time in advance of the scheduled visit. As previously mentioned, the first notification is further based upon one of or any combination of: the medical history of the patient, the insurance network of the patient, where the patient lives and works, the price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient. The first notification may include a message that includes the preference of the patient for having a particular healthcare service related to the scheduled visit performed at a certain time. The first notification may also include a list of facilities that perform a particular healthcare service that is normally performed for the patient. This list of facilities may also be in the insurance network of the patient, within a predetermined area to where the patient lives and works, and/or offer the best value.

In step 216, a second notification is determined based upon the information related to the scheduled visit and the second predetermined time in advance of the scheduled visit. As previously mentioned, the first notification is further based upon one of or any combination of: the medical history of the patient, the insurance network of the patient, where the patient lives and works, the price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient. The second notification may include a message that includes the preference of the patient for having a particular healthcare service related to the scheduled visit performed at a certain time. The second notification may also include a list of facilities that perform a particular healthcare service that is normally performed for the patient. This list of facilities may also be in the insurance network of the patient, within a predetermined area to where the patient lives and works, and/or offer the best value.

In step 218, the mobile device 14 is turned on with the notification application 46 launched and running and the location module 34 running so that the system 10 receives location data of the mobile device 14. In step 220, the notification application 46 determines whether the first predetermined time in advance of the scheduled visit is reached. If the first predetermined time in advance of the scheduled visit is reached, then the system 10 may check in step 222 whether there is an interruption condition. If there is an interruption condition, no notification is outputted to the mobile device 14 and the method goes to step 230. If there is no interruption condition, then in step 224, the messaging system 32 sends the first predetermined notification to the mobile device 14 or the predetermined notification is retrieved from the memory of the mobile device 14.

In step 226, the notification is displayed on the display 38 of the mobile device 14. The notification may include a message button 50 to give an invitation or suggestion or option to initiate a video or audio call or text chat to a qualified person that can help the patient regarding the scheduled visit to the healthcare facility. Alternatively or in addition, other ways to output the message may be provided such as an audio message outputted through the speakers of the mobile device. In step 228, the user may take action based on the displayed message(s).

Figure 12:
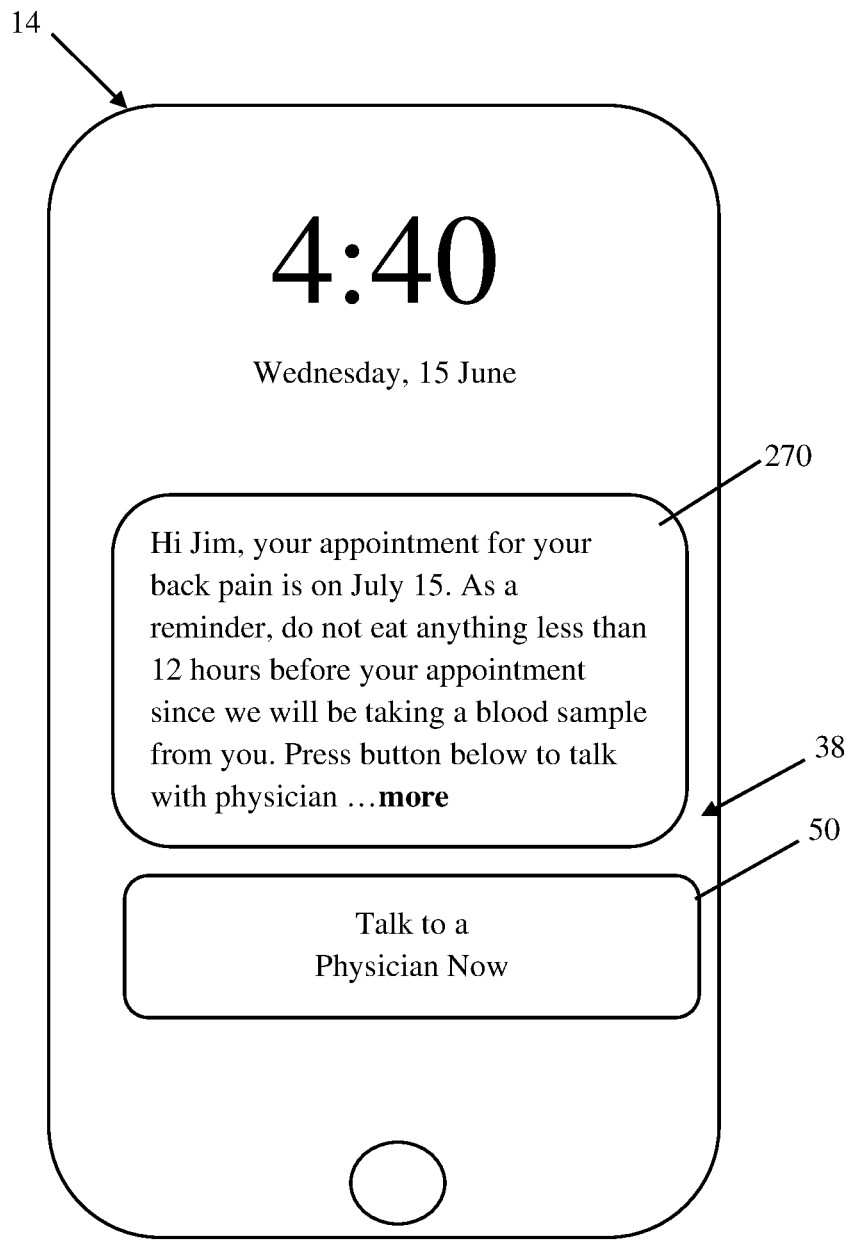
FIG. 12 is a schematic front view of mobile device displaying another message and message button on the display of the mobile device of the system according to FIG. 1.

For example, FIG. 12 shows a first notification that that was sent one month before the scheduled visit for back pain. The first notification includes a reminder message 270 to not eat for less than twelve hours before the visit, since a blood sample will be taken from the patient. The word "more" is also highlighted and if pressed will cause the message to display the entire message for further information about the scheduled visit. Below the first notification is also a message button 50 that gives an invitation or suggestion or option to initiate a video or audio call or text chat to a qualified person that can help the patient regarding the scheduled visit to the healthcare facility. FIG. 5 shows a call being made.

In step 230, the notification application 46 determines whether the second predetermined time in advance of the scheduled visit is reached. If the second predetermined time in advance of the scheduled visit is reached, then the system 10 may check in step 232 whether there is an interruption condition. If there is an interruption condition, no notification is outputted to the mobile device 14 and the method goes to step 240. If there is no interruption condition, then in step 234 (FIG. 11B), the messaging system 32 sends the second predetermined notification to the mobile device 14 or the predetermined notification is retrieved from the memory of the mobile device 14.

In step 236, the second notification is displayed on the display 38 of the mobile device 14. The notification may include a message button 50 to give an invitation or suggestion or option to initiate a video or audio call or text chat to a qualified person that can help the patient regarding the scheduled visit to the healthcare facility. Alternatively or in addition, other ways to output the message may be provided such as an audio message outputted through the speakers of the mobile device. In step 238, the user may take action based on the displayed message(s).

Figure 13:
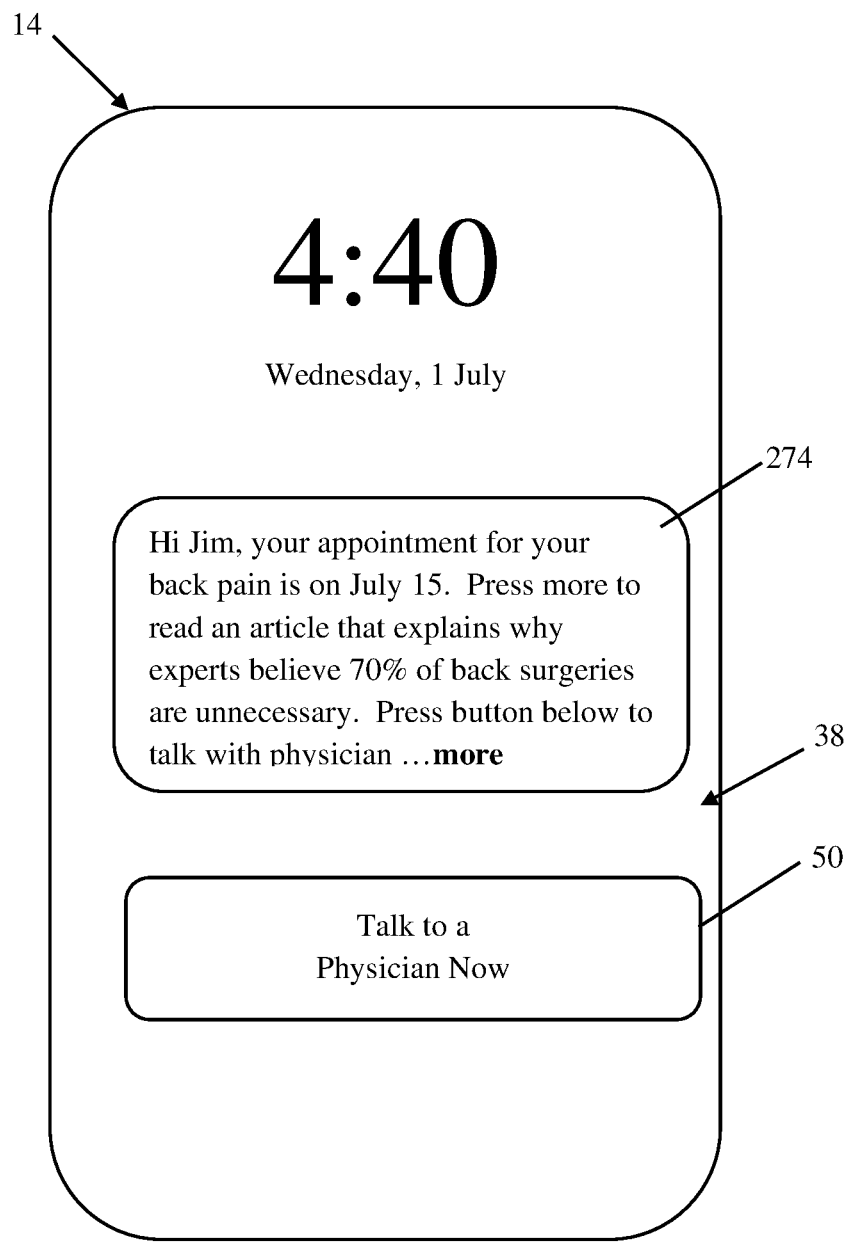
FIG. 13 is a schematic front view of mobile device displaying another message and message button on the display of the mobile device of the system according to FIG. 1.

For example, FIG. 13 shows a second notification that was sent two weeks before the scheduled visit. The second notification includes a message 274 that includes reading material. For example, a patient may have an appointment with an orthopedic surgeon for back pain. The second notification may include a message about an article that explains why experts believe 70% of back surgeries are unnecessary, or what back surgery might be premature if you've tried other procedures to reduce or remove the back pain. Below the second notification is also a message button 50 that gives an invitation or suggestion or option to initiate a video or audio call or text chat to a qualified person that can help the patient regarding the scheduled visit to the healthcare facility. FIG. 5 shows a call being made.

In step 240, a determination is made by the reader module 15 and tracker 17 as mentioned above as to whether the patient has read the first notification or the second notification or both the first and second notifications. If it is determined that the patient has read the first notification or the second notification or both the first and second notifications, then in step 242, a third notification for the next scheduled visit of the patient to the facility is determined. Like the first notification, the third notification is also based upon one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient. However, the third notification also includes more detailed information than the first notification. Alternatively, the third notification may include the same amount of information as the first notification if it is determined that the patient has read the first notification or the second notification or both the first and second notifications.

If it is determined that the patient has not read the first notification or the second notification or both the first and second notifications, then in step 244, a third notification for the next scheduled visit of the patient to the facility is determined. Like the first notification, the third notification is also based upon one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient. However, this third notification includes less information than the first notification. Alternatively, the third notification may include the same amount of information as the first notification if it is determined that the patient has not read the first notification or the second notification or both the first and second notifications.

In step 246 (FIG. 12), information related to a second scheduled visit to the healthcare services facility and any further geofence areas and interruption conditions are created, received, and stored in the data store 30. In step 248, a third predetermined time in advance of the second scheduled visit to the healthcare services facility is determined and store in the data store 30. In step 250, the mobile device 14 is turned on with the notification application 46 launched and running and the location module 34 running so that the system 10 receives location data of the mobile device 14. In step 252, the notification application 46 determines whether the third predetermined time in advance of the scheduled visit is reached. If the third predetermined time in advance of the scheduled visit is reached, then the system 10 may check in step 254 whether there is an interruption condition. If there is no interruption condition, then in step 256, the messaging system 32 sends the third notification to the mobile device 14 or the third notification is retrieved from the memory of the mobile device 14.

In step 258, the third notification is displayed on the display 38 of the mobile device 14. The third notification may include a message button 50 to give an invitation or suggestion or option to initiate a video or audio call or text chat to a qualified person that can help the patient regarding the scheduled visit to the healthcare facility. Alternatively or in addition, other ways to output the message may be provided such as an audio message outputted through the speakers of the mobile device. In step 260, the user may take action based on the displayed message(s).

Figure 14:
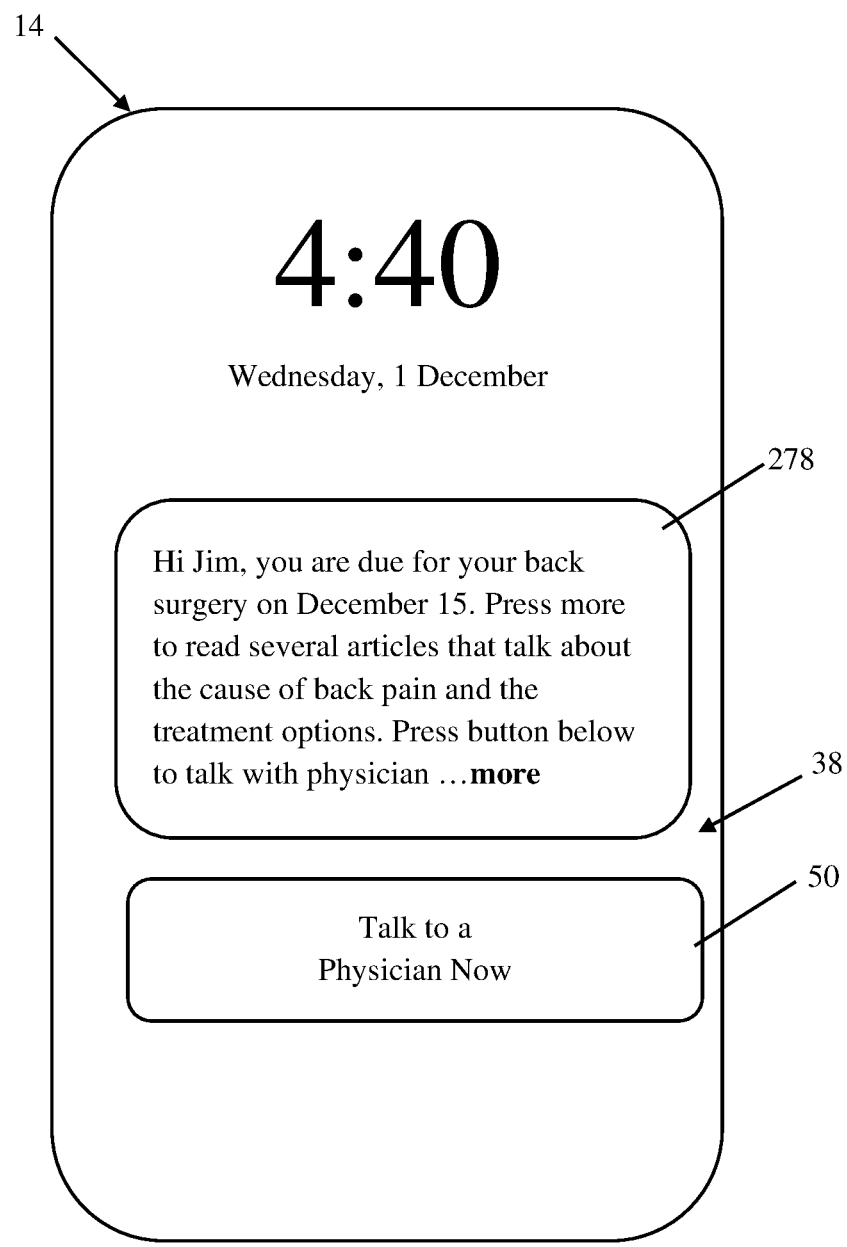
FIG. 14 is a schematic front view of mobile device displaying another message and message button on the display of the mobile device of the system according to FIG. 1.

For example, FIG. 14 shows a notification on a cell phone for a second scheduled visit that includes a more detailed message 278 with further information than the first notification after determining that the patient read the first notification. Below the first notification is also a message button 50 that gives an invitation or suggestion or option to initiate a video or audio call or text chat to a qualified person that can help the patient regarding the scheduled visit to the healthcare facility. FIG. 5 shows a call being made.

If there is an interruption condition, no notification is outputted to the mobile device 14 and the method ends. An example illustrating the method 200 is as follows. A patient has a scheduled appointment with an orthopedist at a healthcare facility. The patient reaches a first predetermined time in advance of the scheduled visit of the orthopedist. Based on the claims and medical history, the system determines that it is a new episode of care for the patient. The system has information in the system that a certain percentage of new episode visits to an orthopedist result in an imaging order. Therefore, the system lists a list of imaging centers in the patient's insurance network, that is in closest to the patient's home and place of work and that offer the best value as the patient walks into the orthopedist's office. Or, for example, when the patient reports for his or her annual dental cleaning and exam, the first notification may include a message that reminds the patient that the patient had x-rays only a year ago and in the preferences of the patient, the patient only wanted x-rays every other year. Thus, the patient is reminded of his or her choice that the patient had the x-rays just a year ago.

Figure 15A:
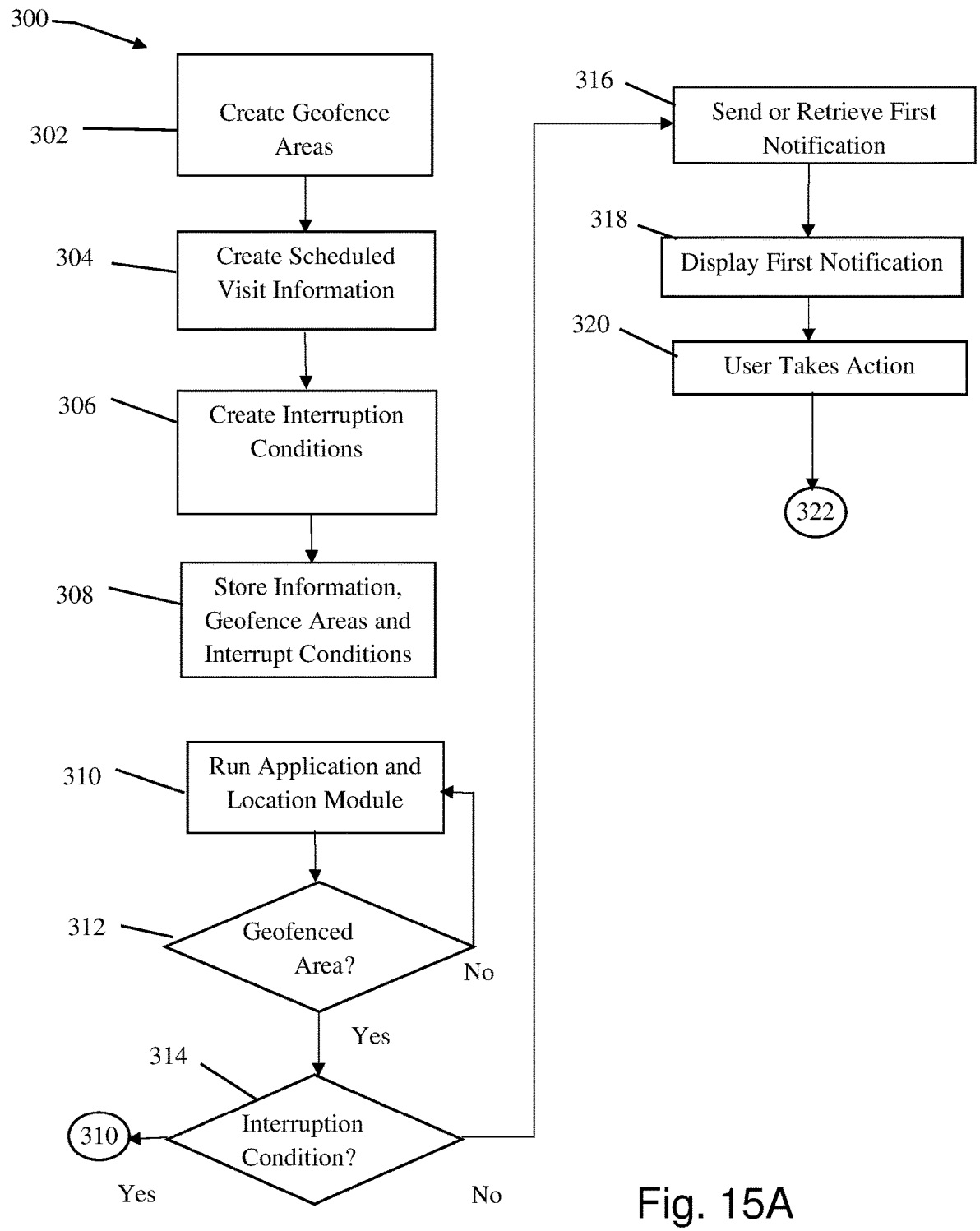
FIGS. 15A and 15B are in combination a flow diagram of another exemplary method according to FIG. 1.
Figure 15B:
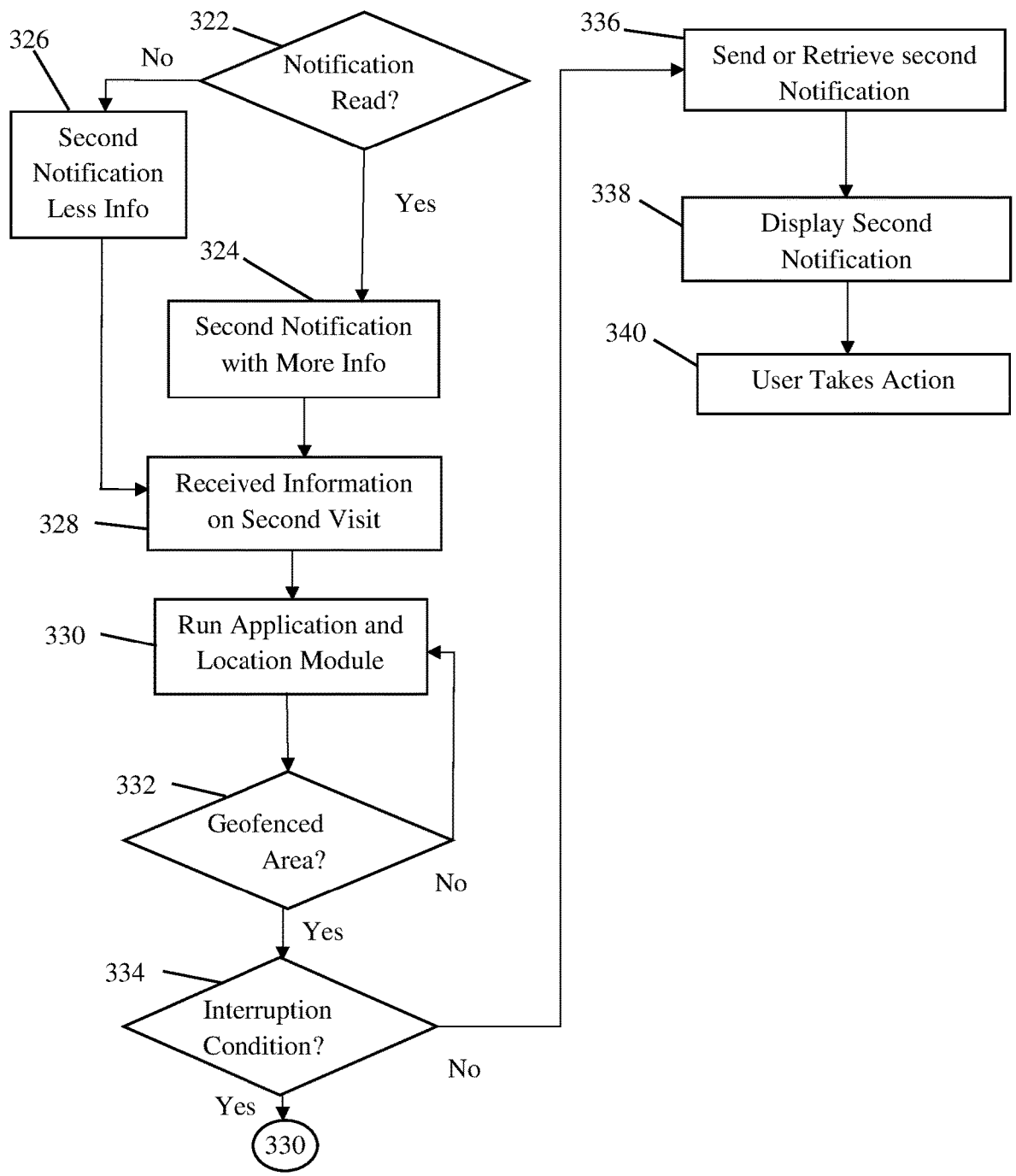

With reference now to FIGS. 15A and 15B, an example methodology 300 is illustrated and described. While the methodology is described as being a series of acts or steps that are performed in a sequence, it is to be understood that the methodology is not limited by the order of the sequence. For instance, some acts or steps may occur in a different order than what is described herein. In addition, a step may occur concurrently with another step. Furthermore, in some instances, not all steps may be required to implement a methodology described herein.

Moreover, the steps or acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodology may be stored in a computer-readable medium, displayed on the display device, and/or the like.

In each step of this sequence of client-server message exchanges, a computer may process a request and return data. In step 302, the geofenced areas are created using the mapping module 24 based on data in the data store 30. One or more of the geofenced areas created may correspond to or be associated with the mobile device 14 associated with the patient and a location that has the facility 31. The facility 31 may offer one or more preventative healthcare services or one or more healthcare services. For example, one geofenced area 26 may be created for the facility 31 as shown in FIG. 6. In another example, a first group of geofenced areas 26a-26d may be created to correspond to the facility 31 as shown in FIG. 7. For example, a location such as an emergency room or an area that screens for cancer on a hospital campus may have several geofenced areas, since one large geofenced area encircling that location would not work, because there may be too many false triggers for people going to the hospital for other purposes. Further, there may be cases where there are one or more parking lots, driveways or entrances that are exclusively for that location, so these parking lots and other such locations would be associated with a geofenced area for that location.

In step 304, information related to a scheduled visit to the healthcare facility 31 by the patient associated with the mobile device 14 is created and stored in the data store 30. In step 306, the interruption conditions for preventing the outputting of the notification when the location data of the mobile device 14 is determined to be within the geofenced area may be created using the mapping module 24. In step 308, the information related to the scheduled visit to the healthcare services facility 31 by the patient associated with the mobile device 14, the geofenced areas, and any interruption conditions are stored in the data store 30.

In step 310, the mobile device 14 is turned on with the notification application 46 launched and running and the location module 34 running so that the system 10 receives location data of the mobile device 14. In step 312 the notification application 46 determines when the mobile device 14 is located within a geofenced area associated with the facility 31 stored in the data store 30. If the mobile device 14 is located within the geofenced area, then the system 10 may check in step 314 whether there is an interruption condition for that geofenced area. If there is an interruption condition, no notification is outputted to the mobile device 14 and the method goes back to step 310 to continue to receive location data of the mobile device 14.

If the mobile device 14 is located within the geofenced area and there is no interruption condition, then in step 316, the messaging system 32 sends the first notification to the mobile device 14 or the first notification is retrieved from the memory of the mobile device 14. The first notification includes information about the first scheduled visit and based upon one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient. The first notification may include a message that includes the preference of the patient for having a particular healthcare service related to the scheduled visit performed at a certain time. The first notification may also include a list of facilities that perform a particular healthcare service that is normally performed for the patient. This list of facilities may also be in the insurance network of the patient, within a predetermined area to where the patient lives and works and/or offer the best value.

In step 318, the notification is displayed on the display 38 of the mobile device 14. The notification may include a message button 50 to give the option to place an audio or video call with a qualified healthcare professional an invitation or suggestion to initiate a video or audio call to a qualified person that can help the patient regarding the unscheduled visit. In step 320, the user may take action based on the displayed message(s).

In step 322, a determination is made by the reader module 15 and tracker 17 as mentioned above as to whether the patient has read the first notification. If it is determined that the patient has read the first notification, then in step 324 (FIG. 15B), a second notification for the next scheduled visit of the patient to the facility is determined. Like the first notification, the second notification is also based upon one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient. However, this second notification also includes more detailed information than the first notification. Alternatively, the second notification may include the same amount of information as the first notification if it is determined that the patient has read the first notification.

If it is determined that the patient has not read the first notification, then in step 326, a second notification for the next scheduled visit of the patient to the facility is determined. Like the first notification, the second notification is also based upon one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient. However, this second notification also includes less information than the first notification. Alternatively, the second notification may include the same amount of information as the first notification if it is determined that the patient has not read the first notification.

In step 328, information related to a second scheduled visit to the healthcare services facility 31 is received. In step 330, the mobile device 14 is turned on with the notification application 46 launched and running and the location module 34 running so that the system 10 receives location data of the mobile device 14. In step 332 the notification application 46 determines when the mobile device 14 is located within a geofenced area associated with the facility 31 stored in the data store 30. If the mobile device 14 is located within the geofenced area, then the system 10 may check in step 334 whether there is an interruption condition for that geofenced area. If there is an interruption condition, no notification is outputted to the mobile device 14 and the method goes back to step 330 to continue to receive location data of the mobile device 14.

If the mobile device 14 is located within the geofenced area and there is no interruption condition, then in step 336, the messaging system 32 sends the second notification to the mobile device 14 or the second notification is retrieved from the memory of the mobile device 14. In step 8 the second notification is displayed on the display 38 of the mobile device 14. The notification may include a message button 50 to give the option to place an audio or video call with a qualified healthcare professional an invitation or suggestion to initiate a video or audio call to a qualified person that can help the patient regarding the scheduled visit. In step 340, the user may take action based on the displayed message(s).

For example, FIG. 14 shows a notification on a cell phone for a second scheduled visit that includes a more detailed message 278 with further information than the first notification after determining that the patient read the first notification. Below the first notification is also a message button 50 that gives an invitation or suggestion or option to initiate a video or audio call or text chat to a qualified person that can help the patient regarding the scheduled visit to the healthcare facility. FIG. 5 shows a call being made.

An example illustrating the method 300 is as follows. A patient has a scheduled appointment with an orthopedist at a healthcare facility. The patient crosses a geofence area. Based on the claims and medical history, the system determines that it is a new episode of care for the patient. The system has information in the system that a certain percentage of new episode visits to an orthopedist result in an imaging order. Therefore, the system lists a list of imaging centers in the patient's insurance network, that is in closest to the patient's home and place of work and that offer the best value as the patient walks into the orthopedist's office. Or, for example, when the patient reports for his or her annual dental cleaning and exam, the first notification may include a message that reminds the patient that the patient had x-rays only a year ago and in the preferences of the patient, the patient only wanted x-rays every other year. Thus, the patient is reminded of his or her choice that the patient had the x-rays just a year ago. Optionally, a determination may be made as to whether the patient has read the first notification. Then, a second notification may be created for the next scheduled visit or for this scheduled visit having information based on this determination. For example, the second notification may include more information if the patient read the first notification and less information if the patient did not read the first notification.

Another example may be that the patient walks into an orthopedist's office and as the patient is walking in, the patient receives a list of independent imaging centers closest to his or her home and place of work (and perhaps along the route between the two). The patient receives this information because the system uses the location module to determine that the patient is in close to the orthopedist's office and the system determines from its datastore that the patient has an appointment with an orthopedist. The system may also know it's a first visit by accessing the medical history and\or claims history and determine that the patient has not been to an orthopedist in five years. That, combined with data that determines that first visits to an orthopedist have an X % chance of an imaging order prompts the system to send the patient the list of facilities that are in the patient's network and are conveniently located. Also, the messaging system may send a message or otherwise tell the patient that the facility can take the patient for the service in the next 24 hours.

In another example, a patient is scheduled to see a neurologist because the patient believes that he or she may have multiple sclerosis. The system may send three articles to read a week before the patient's appointment, based on the patient's individual knowledge, skill and confidence or reading ability. Then the system may send a a second piece of information to the patient as the patient pulls into the parking lot. This information might include the six most important questions to ask the doctor.

The system and method reminds and encourages patients to seek preventative healthcare or other unscheduled healthcare services when they are in the vicinity of a facility that offers such care. The system and method conveniently notifies the patient when they are in the vicinity of the facility and provides further information to the patient to help the patient make a decision as to whether to use the facility to perform the healthcare service. The system and method may also prevent notifying the patient when they are in the vicinity of the location based on certain conditions.

The system and method also provides information quickly and conveniently to patients who seek immediate medical attention when they are approaching a healthcare facility and also to the medical professions involved with the patient, which also saves costs and time to diagnose and treat the medial condition of the patient and process the medical information. The system also provides information to the patient before a certain time in advanced of a scheduled visit. The system also provides more or less information based on whether the patient has read or not the previous message. Although various embodiments of the disclosed system and method for providing notifications to a user have been shown and described, modifications may occur to those skilled in the art upon reading the specification. The present application includes such modifications and is limited only by the scope of the claims.

What is claimed is:

1. A computer-implemented method for providing notifications and communication to a patient based on a first scheduled visit to a healthcare services facility, the method comprising the following operations performed by at least one computer processor:
   a) receiving information related to the first scheduled visit to the healthcare services facility, wherein a mobile device is associated with the patient;
   b) storing the information related to the first scheduled visit to the healthcare services facility in a data store;
   c) sending a first notification to or retrieving the first notification from the mobile device, wherein the first notification includes information about the first scheduled visit and is based upon the location of the healthcare services facility and patient and a geofenced area indicating that the patient is in close proximity to the healthcare services facility when entered into by the mobile device associated with the patient and one of or any combination of: the medical history of the patient, the insurance network of the patient, where the patient lives and works, price information of the healthcare service being performed for the patient, preferences of the patient, the knowledge and skill and self-confidence of the patient to manage healthcare;
   d) outputting the first notification to the mobile device;
   e) determining whether the patient has read the first notification;
   f) receiving information related to a second scheduled visit of the patient to the healthcare services facility;
   g) sending a second notification to or retrieving the second notification from the mobile device, wherein the second notification includes information about the second scheduled visit and is based upon the location of the healthcare services facility and patient and a geofenced area indicating that the patient is in close proximity to the healthcare services facility when entered into by the mobile device associated with the patient, wherein the second notification includes more or less information based on determining whether the patient has read the first notification; and
   h) outputting the second notification to the mobile device.

2. The computer-implemented method of claim 1, wherein the second notification includes more information than the first notification in response to determining that the patient has read the first notification.

3. The computer-implemented method of claim 1, wherein the second notification includes less information than the first notification in response to determining that the patient has not read the first notification.

4. The computer-implemented method of claim 1, wherein the second notification includes information about the second scheduled visit and one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient.

5. The computer-implemented method of claim 1, wherein one of the first notification and the second notification or both the first notification and the second notification further includes an invitation or suggestion to initiate a video or audio call or text chat to a qualified person that can help the patient regarding the first scheduled visit to the healthcare facility.

6. The computer-implemented method of claim 1, wherein the first notification is outputted to the mobile device upon determining that the mobile device has crossed or entered at least one geofenced area associated with the mobile device.

7. The computer-implemented method of claim 6, wherein the first notification includes a list of facilities that perform the healthcare service for the patient.

8. The computer-implemented method of claim 7, wherein the list of facilities are in the insurance network of the patient and are within a predetermined area to where the patient lives or works and offer the best value.

9. The computer-implemented method of claim 1, wherein the first notification includes the preference of the patient for having a particular healthcare service related to the first scheduled visit performed at a certain time.

10. The computer-implemented method of claim 9, wherein the first notification is outputted to the mobile device upon determining that the mobile device has crossed or entered at least one geofenced area associated with the mobile device.

11. The computer-implemented method of claim 1, wherein determining whether the patient has read the first notification includes tracking the activation of a tracking code by the patient touching a tracking image.

12. The computer-implemented method of claim 1, wherein determining whether the patient has read the first notification includes using a web tracking device, wherein the web tracking device is one of cookies and web beacons or both the cookies and web beacons.

13. The computer-implemented method of claim 5, wherein the first notification further includes an invitation or suggestion to initiate a video or audio call or text chat by displaying a button on a display of the mobile device to be pressed for initiating the video or audio call to a qualified person that can help the patient regarding the first scheduled visit to the healthcare facility upon pressing the button.

14. The computer-implemented method of claim 1 further comprising:
- i) determining a first predetermined time in advance of the first scheduled visit and a second predetermined time in advance of the first scheduled visit, wherein the second predetermined time is different than the first predetermined time, wherein the first notification is sent to or retrieved from the mobile device when the first predetermined time in advance of the first scheduled visit is reached;
- j) determining a third notification based upon the information related to the first scheduled visit and the second predetermined time in advance of the first scheduled visit, wherein the third notification is further based upon one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient;
- k) sending the third notification to or retrieving the third notification from the mobile device when the second predetermined time in advance of the first scheduled visit is reached; and
- l) outputting the third notification to the mobile device when the second predetermined time in advance of the first scheduled visit is reached.

15. A non-transitory computer-readable storage medium storing executable instructions for providing notifications and communication to a patient based on a first scheduled visit to a healthcare services facility that, as a result of being executed by one or more processors of a computer system, cause the computer system to at least:
- a) receive information related to the first scheduled visit to the healthcare services facility, wherein a mobile device is associated with the patient;
- b) store the information related to the first scheduled visit to the healthcare services facility in a data store;
- c) send a first notification to or retrieving the first notification from the mobile device, wherein the first notification includes information about the first scheduled visit and is based upon the location of the healthcare services facility and patient and a geofenced area indicating that the patient is in close proximity to the healthcare services facility when entered into by the mobile device associated with the patient and one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient;
- d) output the first notification to the mobile device;
- e) determine whether the patient has read the first notification;
- f) receive information related to a second scheduled visit of the patient to the healthcare services facility;
- g) send a second notification to or retrieving the second notification from the mobile device, wherein the second notification includes information about the second scheduled visit and is based upon the location of the healthcare services facility and patient and a geofenced area indicating that the patient is in close proximity to the healthcare services facility when entered into by the mobile device associated with the patient, wherein the second notification includes more or less information based on determining whether the patient has read the first notification; and
- h) output the second notification to the mobile device.

16. The non-transitory computer-readable storage medium of claim 15, wherein the second notification includes more information than the first notification in response to determining that the patient has read the first notification.

17. The non-transitory computer-readable storage medium of claim 15, wherein the second notification includes less information than the first notification in response to determining that the patient has not read the first notification.

18. The non-transitory computer-readable storage medium of claim 15, wherein the second notification includes information about the second scheduled visit and one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient.

19. The non-transitory computer-readable storage medium of claim 15 further comprising causing the computer system to at least:
- i) determine a first predetermined time in advance of the first scheduled visit and a second predetermined time in advance of the first scheduled visit, wherein the second predetermined time is different than the first predetermined time, wherein the first notification is sent to or retrieved from the mobile device when the first predetermined time in advance of the first scheduled visit is reached;
- j) determine a third notification based upon the information related to the first scheduled visit and the second predetermined time in advance of the first scheduled visit, wherein the third notification is further based upon one of or any combination of: the medical history of the patient, the insurance network of the patient, where the patient lives and works, price information of the healthcare service being performed for the patient, preferences of the patient, the knowledge and skill and self-confidence of the patient to manage healthcare, and the location of the healthcare services facility and patient and a geofenced area indicating that the patient is in close proximity to the healthcare services facility when entered into by the mobile device associated with the patient;

k) send the third notification to or retrieving the third notification from the mobile device when the second predetermined time in advance of the first scheduled visit is reached; and l) output the third notification to the mobile device when the second predetermined time in advance of the scheduled visit is reached.

* * * * *